Figure 1:
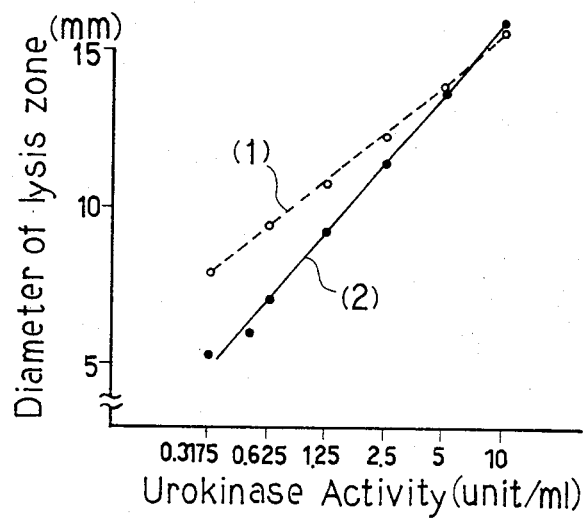

United States Patent [19]

Miyazaki et al.

[11] Patent Number: 4,536,391
[45] Date of Patent: Aug. 20, 1985

[54] PROCESS FOR PREPARING UROKINASE COMPLEX

[75] Inventors: Wasei Miyazaki; Tsuneo Sato; Yasuo Nakayama; Tadao Sato, all of Tokushima, Japan

[73] Assignee: Otsuka Pharmaceutical Co., Japan

[21] Appl. No.: 551,841

[22] Filed: Nov. 15, 1983

[30] Foreign Application Priority Data

Nov. 17, 1982 [JP] Japan .................................. 57-202359
Apr. 28, 1983 [JP] Japan .................................. 58-75198

[51] Int. Cl.³ .................... A61K 37/48; A61K 37/00; C07G 7/00; C12N 9/72
[52] U.S. Cl. ................................. 424/94; 435/215; 514/2; 260/112 R
[58] Field of Search .................. 435/215; 424/177, 94; 260/112 R

[56] References Cited

U.S. PATENT DOCUMENTS 4,029,767  6/1977  Vairel et al. ........................ 435/215
4,349,630  9/1982  Maximenko et al. ............... 435/215

Primary Examiner—Blondel Hazel
Attorney, Agent, or Firm—Larson and Taylor

[57] ABSTRACT

This invention provides a process for preparing a fibrin-adsorable protein-urokinase complex characterized by reacting a protein adsorbable by fibrin with urokinase in the presence of a protein coupling reagent represented by the formula

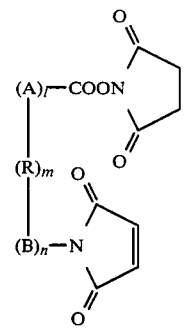

wherein R is phenylene or cycloalkylene, A is lower alkylene, B is lower alkylene which may optionally be substituted by lower alkylthio or phenyl-lower alkylthio, and l, m and n are each 0 or 1 provided that l, m and n are not 0 at the same time.

The complex is useful as a thrombolytic agent.

17 Claims, 2 Drawing Figures

PROCESS FOR PREPARING UROKINASE COMPLEX

This invention relates to a process for preparing novel fibrin-adsorbable protein-urokinase complexes.

Urokinase, a thrombolytic enzyme, is widely used for clinical purposes as an agent for treating thrombosis. However, urokinase is not capable of being adsorbed by fibrin which is a protein component of thrombi, and, when intravenously given, is rapidly metabolized and excreted, so that the enzyme fails to achieve as high a therapeutic effect as is expected from its activity in vitro. When urokinase is administered at large doses as practiced in the U.S. and European countries, systemic activation of plasminogen takes place, accompanied by marked side effects such as a tendency of bleeding due to the decomposition of fibrinogen. On the other hand, the circulating blood contains large amounts of plasmin inhibitors, such as $\alpha_2$-plasmin inhibitor and $\alpha_2$-macroglobulin, which inhibit the thrombolysis of urokinase due to the activation (formation) of plasmin.

In view of the above, we directed attention to the possibility of coupling a fibrin-adsorbable protein (i.e., a protein adsorbable by fibrin) with urokinase to give urokinase ability to couple with fibrin because urokinase will then be adsorbed to thrombi as contemplated for therapy with reduced susceptibility to metabolism and excretion to result in a prolonged halflife period thereof in the blood and further because urokinase as coupled with fibrin will be less prone to the action of plasmin inhibitors to achieve enhanced therapeutic effect while permitting plasminogen to be locally activated at the site of thrombus and consequently alleviating bleeding tendency and like side effects. Thus, in order to obtain urokinase adsorbable by fibrin, we have carried out intensive research and developed a complex with use of a heavy chain derived from plasmin and serving as a fibrin-adsorbable protein (the heavy chain will hereinafrer be referred to as "plasmin HC") by coupling the plasmin HC with urokinase by means of a specific protein coupling reagent. We have found that this complex has ability to be adsorbed by fibrin, possesses the desired activity of urokinase and is effective as a novel thrombolytic agent. The present invention has been accomplished based on this novel finding.

Stated more specifically, this invention provides a process for preparing a fibrin-adsorbable protein-urokinase complex which process is characterized by reacting a fibrin-adsorbable protein with urokinase in the presence of a protein coupling reagent represented by the formula

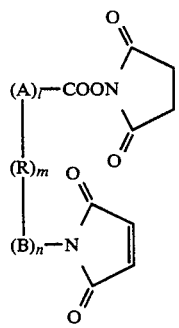

(1)

wherein R is phenylene or cycloalkylene, A is lower alkylene, B is lower alkylene which may optionally be substituted by lower alkylthio or phenyl-lower alkylthio, and l, m and n are each 0 or 1 provided that l, m and n are not 0 at the same time.

The complex obtained by the above process of this invention acts selectively (locally) on the site of thrombus when used as a thrombolytic agent in a smaller amount than when urokinase is used singly, undergoes retarded metabolism and excretion, is less affected by plasmin inhibitors, exhibits sustained satisfactory thrombolytic activity and is less likely to entail side effects such as tendency of systemic bleeding, hence very effective. Furthermore, the complexes of the invention have an additional effect that the fibrinolytic activity thereof is potentiated in the presence of fibrin-like substances. Therefore, the complexes of the invention have a fibrinolytic effect as produced by tissue-type plasminogen activators. Thus, the present invention has established a novel process of easily and efficiently producing such a novel complex which is useful as a thrombolytic agent, contributing a great deal to the pharmaceutical industry and other fields.

In the compounds of the formula (1) useful as protein coupling reagents for the present process, examples of phenylene groups represented by R are o-phenylene, m-phenylene and p-phenylene, and examples of cycloalkylene groups similarly represented are cyclopropylene, 1,3-cyclobutylene, 1,2-cyclopentylene, 1,3-cyclopentylene, 1,2-cyclohexylene, 1,4-cyclohexylene, 1,3-cycloheptylene, 1,5-cyclooocytylene and like cycloalkylene groups having 3 to 8 carbon atoms.

Examples of lower alkylene groups represented by A are methylene, ethylene, trimethylene, tetramethylene, pentamethylene, hexamethylene, 2-methyltrimethylene and like alkylene groups having 1 to 6 carbon atoms. Examples of lower alkylene groups which are represented by B and which may optionally be substituted by lower alkylthio or phenyl-lower alkylthio are alkylene groups having 1 to 6 carbon atoms and exemplified above, and alkylene groups having 1 to 6 carbon atoms and substituted with lower alkylthio having 1 to 6 carbon atoms or with phenyl-lower alkylthio wherein the alkyl moiety has 1 to 6 carbon atoms. Examples of the lower alkylene substituted with lower alkylthio are methylthiomethylene, ethylthiomethylene, butylthiomethylene, hexylthiomethylene, ethylthioethylene, propylthioethylene, 2-methylthiotrimethylene, 2-ethylthioethylmethylene, 2-propylthiotetramethylene, 3-ethylthiomethylpentamethylene, 3-ethylthiohexamethylene, etc. Examples of the lower alkylene substituted with phenyl-lower alkylthio are benzylthiomethylene, benzylthiomethylmethylene, benzylthioethylene, 2-benzylthiotrimethylene, 2-benzylthioethylethylene, 2-[2-(2-phenylethylthio)ethyl]trimethylene, 3-phenylpropylthiomethylene, 4-phenylbutylthioethylene, 3-phenylpentylthiomethylene, 6-phenylhexylthioethylene, 3-benzylthiopropylethylene, 2-benzylthiomethylpentamethylene, 3-benzylthiohexamethylene, etc.

The compounds represented by the formula (1) include known or novel compounds which can be easily prepared, for example, by the process disclosed in T.Kitagawa et al., J.Biochem. (Tokyo), 79, 233 (1976). For example, such compounds are prepared by a process represented by the following equation-1.

Equation-1

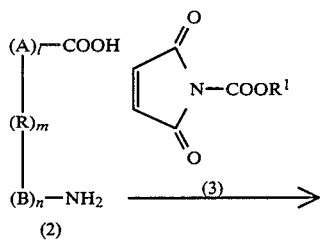

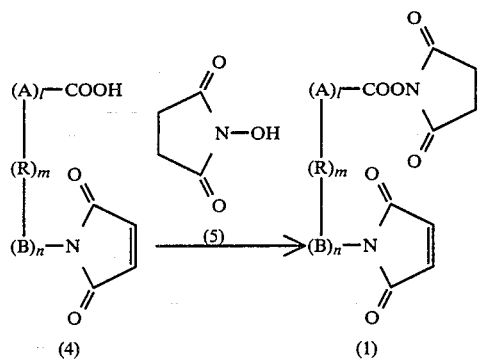

In the above equation, R, A, B, l, m and n are as defined above, and R¹ is lower alkyl.

The reaction between an aminocarboxylic acid of the formula (2) and a maleimide derivative of the formula (3) is carried out in a suitable solvent in the presence of a basic compound. Examples of useful basic compounds are potassium carbonate, sodium hydrogen carbonate, sodium hydride, sodium carbonate, sodium hydroxide, potassium hydroxide, potassium hydrogen carbonate and like inorganic bases. The solvent can be any of inert solvents which will not adversely affect the reaction. Typical of such solvents are water; methanol, ethanol, propanol, butanol, ethylene glycol and like alcohols; dimethyl ether, tetrahydrofuran (THF), dioxane, monoglyme, diglyme and like ethers; acetone, methyl ethyl ketone and like ketones N,N-dimethylformamide (DMF), dimethyl sulfoxide (DMSO), hexamethylphosphoric triamide (HMPA) and like aprotic polar solvents; etc. The ratio between the aminocarboxylic acid (2) and the maleimide derivative (3) is not particularly limited, but is variable over a wide range. Usually about 1 to about 3 moles, preferably about 1 to about 1.3 moles, of the latter is used per mole of the former. The reaction temperature, which is not particularly limited either, is usually about 0 to about 50° C., preferably about 0 to about 30° C. The reaction time is usually about 1 to about 3 hours. The reaction thus conducted affords a compound of the formula (4).

The compound of the formula (4) can also be obtained with use of maleic anhydride in place of the maleimide derivative (3) by reacting maleic anhydride with the aminocarboxylic acid (2) and subjecting the resulting maleic acid derivative to a dehydration reaction. Such reaction is carried out by using about 1 to about 3 moles, preferably about 1 to about 1.3 moles, of maleic anhydride per mole of the aminocarboxylic acid (3) and using the same solvent as in the reaction between the aminocarboxylic acid (2) and the maleimide derivative (3). The reaction is conducted at a temperature usually of about 20 to about 150° C., preferably about 30 to about 100° C., for about 1 to about 5 hours. The maleic acid derivative obtained can be subjected, as contained in the reaction mixture, to the subsequent dehydration reaction without being isolated therefrom and purified. This reaction is carried out in the presence of a dehydration condensation agent without using any solvent or with use of a suitable solvent. Examples of useful dehydration condensation agents are acetic anhydride, propionic anhydride, butyric anhydride, caproic anhydride, benzoic anhydride and like acid anhydrides. Examples of suitable solvents are dimethyl ether, THF, dioxane, monoglyme, diglyme and like ethers; benzene, toluene, xylene and like aromatic hydrocarbons; methylene chloride, chloroform and like hydrocarbon halides; etc. The amount of dehydration condensation agent, which is not limited particularly, is usually at least a catalytic amount, preferably about 10 to about 100 moles per mole of the maleic acid derivative. A large excess of the agent can be used to serve also as a solvent. The dehydration reaction is conducted usually at about 50 to about 150° C., preferably at about 90 to about 100° C., for about 1 to about 5 hours.

The desired maleimide derivative of the formula (1) is obtained by reacting the compound of the formula (4) thus prepared with N-hydroxysuccinimide (5). This reaction is conducted in a suitable solvent, preferably in the presence of a dehydration condensation agent. Examples of useful dehydration condensation agent are dicyclohexylcarbodiimide (DCC), trichloroacetonitrile, acetylene ethyl ether, ethyl cyanate, etc. Examples of useful solvents are diethyl ether, THF, dimethoxyethane (DME), diglyme and like ethers; DMF, pyridine, 2-methylpyrrolidone, etc. The amount of N-hydroxysuccinimide (5) to be used based on the compound of the formula (4) is not limited particularly; usually about 1 to about 3 moles, preferably about 1 to about 1.3 moles, of the imide is used per mole of the latter. The reaction is carried out generally at about 0 to about 50° C., preferably about 0 to about 30° C., for about 1 to about 3 hours. When the dehydration condensation agent is used for the reaction, usually about 1 to about 3 moles, preferably about 1 to about 1.3 moles, of the agent is used per mole of the compound (4).

In place of the compound of the formula (4), also usable for the above reaction is like compound having its carboxyl group activated. Examples of such compounds are mixed acid anhydrides which are obtained by reacting the compound (4) with alkylhalocarboxylic acids, and acid halides thereof.

The process wherein the mixed acid anhydride is used is practiced usually by reacting the compound of the formula (4) with an alkylhalocarboxylic acid, such as methyl chloroformate, methyl bromoformate or isobutyl chloroformate, by Schotten-Baumann reaction and reacting N-hydroxysuccinimide (5) with the resulting mixed acid anhydride as contained in the reaction mixture without isolation. The Schotten-Baumann reaction is carried out in the presence of a basic compound which is usually used for the reaction, at about -20 to about 100° C., preferably about 0 to about 50° C., for about 5 minutes to about 10 hours. Examples of useful basic compounds are sodium hydroxide, potassium hydroxide, sodium carbonate, potassium carbonate, sodium hydrogen carbonate, potassium hydrogen carbonate, silver carbonate and like inorganic bases; sodium methylate, sodium ethylate and like alcoholates; and trimethylamine, triethylamine, pyridine, N,N-dimethylaniline, N-methylmorpholine, 4-dimethylaminopyridine, 1,5-diazabicyclo[4,3,0]non-5-ene (DBN), 1,8-diazabicyclo[5,4,0]undec-7-ene (DBU), 1,4- diazabicyclo[2,2,2]octane (DABCO) and like organic bases. The reaction between the resulting mixed acid anhydride and N-hydroxysuccinimide (5) is conducted usually in a suitable solvent at about −20° to about 150° C., preferably about 10 to about 50° C., for about 5 minutes to about 10 hours. Examples of suitable solvents are those generally used for such mixed acid anhydride processes, such as methylene chloride, chloroform, dichloroethane and like hydrocarbon halides; benzene, toluene, xylene and like aromatic hydrocarbons; diethyl ether, THF, DME and like ethers; methyl acetate, ethyl acetate and like esters; DMF, DMSO, HMPA and like aprotic polar solvents, etc. Usually the compounds of the formula (4), alkylhalocarboxylic acid and N-hydroxysuccinimide (5) are used in approximately equimolar amounts. Preferably about 1 to about 1.5 moles of each of the latter two compounds i.e., alkylhalocarboxylic acid and N-hydroxysuccinimide (5) is used per mole of the compound of the formula (4).

The process wherein the acid halide is used is practiced usually by reacting a halogenating agent with the compound of the formula (4) and reacting N-hydroxysuccinimide (5) with the resulting carboxylic acid halide as contained in the reaction mixture without isolation. The reaction between the compound of the formula (4) and the halogenating agent is conducted in the presence or absence of a solvent. Examples of useful solvents are those which will not adversely affect the reaction, such as benzene, toluene, xylene and like aromatic hydrocarbons; chloroform, methylene chloride, carbon tetrachloride and like hydrocarbon halides; dioxane, THF, diethyl ether and like ethers; DMF, DMSO and the like. The halogenating agent can be a usual halogenating agent which converts the hydroxyl of the carboxyl group to a halogen, such as thionyl chloride, phosphorus oxychloride, phosphorus oxybromide, phosphorus pentachloride, phosphorus pentabromide or the like. The ratio between the compound of the formula (4) and the halogenating agent to be used is not limited particularly but is suitable determined. When the reaction is conducted in the absence of a solvent, a large excess of the latter is usually used relative to the former, while in the presence of a solvent, usually at least about one mole, preferably about 2 to about 4 moles, of the latter is used per mole of the former. The reaction, the conditions of which are not limited particularly, is conducted usually at room temperature to about 100° C., preferably about 50 to about 80° C., for about 30 minutes to about 6 hours. The reaction between the resulting carboxylic acid halide and N-hydroxysuccinimide (5) is carried out in the presence of an agent for removing hydrogen halides. Usual basic compounds are used as such agents. Examples of such basic compounds are sodium hydroxide, potassium hydroxide, sodium carbonate, potassium carbonate, sodium hydrogen carbonate, potassium hydrogen carbonate, silver carbonate and like inorganic bases; sodium methylate, sodium ethylate and like alcoholates and triethylamine, pyridine, N,N-dimethylaniline, N-methylmorpholine, 4-dimethylaminopydine, 1,5-diazabicyclo[4,3,0]non-5-ene (DBN), 1,8-diazabicyclo[5,4,0]undec-7-ene (DBU), 1,4-diazabicyclo[2,2,2]octane (DABCO) and like organic bases. The reaction is conducted in the absence or presence of a solvent. The solvent can be any of inert solvents which will not adversely affect the reaction and which include, for example, chloroform, methylene chloride, carbon tetrachloride and like hydrocarbon halides diethyl ether, THF, dioxane and like ethers; benzene, toluene, xylene and like aromatic hydroxycarbons; methyl acetate, ethyl acetate and like esters; DMF, DMSO, HMPA and like aprotic polar solvents; etc. Although the ratio between the carboxylic acid halide and N-hydroxysuccinimide (5) is not limited particularly, at least one mole, preferably about 1 to about 2 moles, of the latter is used per mole of the former when the reaction is conducted in a solvent. The reaction, the conditions of which are not limited particularly, is carried out usually at about −30 to about 100° C., preferably about 0 to about 50° C., for about 0.5 to about 12 hours.

The aminocarboxylic acid represented by the formula (2) in the equation-1 is prepared, for example, by the process represented by the following equation of reaction.

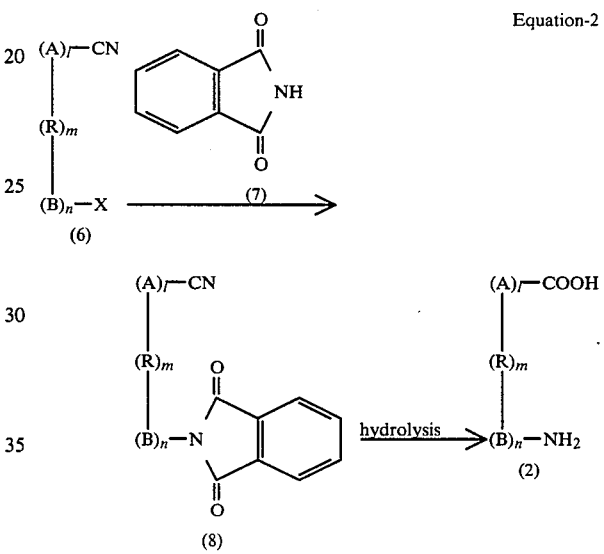

Equation-2

In the above equation, R, A, B, l, m and n are as defined above, X is a halogen atom, alkanesulfonyloxy, arylsulfonyloxy or aralkylsulfonyloxy.

Examples of atoms or groups represented by X in the formula (6) are halogen atoms such as chlorine, bromine and iodine atoms; alkanesulfonyloxy groups such as methanesulfonyloxy, ethanesulfonyloxy, isporopanesulfonyloxy, propanesulfonyloxy, butanesulfonyloxy, tert-butanesulfonyloxy, pentanesulfonyloxy and hexanesulfonyloxy; arylsulfonyloxy groups such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, α- or β-naphthylsulfonyloxy and like substituted or unsubstituted arylsulfonyloxy groups; and aralkylsulfonyloxy groups such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α- or β-naphthylmethylsulfonyloxy and like substituted or unsubstituted aralkylsulfonyloxy groups.

The aminocarboxylic acid represented by the formula (2) is prepared by reacting a known compound of the formula (6) with phthalimide (7) and hydrolyzing the resulting product (8) according to the above equation-2.

The compound of the formula (6) can be reacted with phthalimide (7) under the same conditions as used for the foregoing reaction of carboxylic acid halide with N-hydroxysuccinimide (5).

The compound represented by the formula (8) and obtained as above is hydrolyzed in the absence of solvent or in a suitable solvent such as water, methanol, ethanol, isopropanol or like alcohol, acetic acid or the like, by being subjected to the action of an acid or alkali. Examples of useful acids are hydrochloric acid, sulfuric acid and like mineral acids. Exemplary of useful alkalis are sodium hydroxide, potassium hydroxide, potassium carbonate, sodium carbonate, etc. The acid or alkali is used in an amount of at least 1 mole per mole of the compound of the formula (8). Usually it is used in an excessively larger amount. The reaction is conducted usually at room temperature to about 150° C., preferably about 50 to about 100° C., generally for about 0.5 to about 24 hours. The hydrolysis reaction for converting the phthalimido group to an amino group can be conducted preferably in the same solvent as above under similar reaction conditions in the presence of at least an equimolar amount of hydrazine.

Some of the aminocarboxylic acid of the formula (2) and the compounds of the formula (6) for preparing the acid can be prepared also by the processes represented by the following equations-3 to -5.

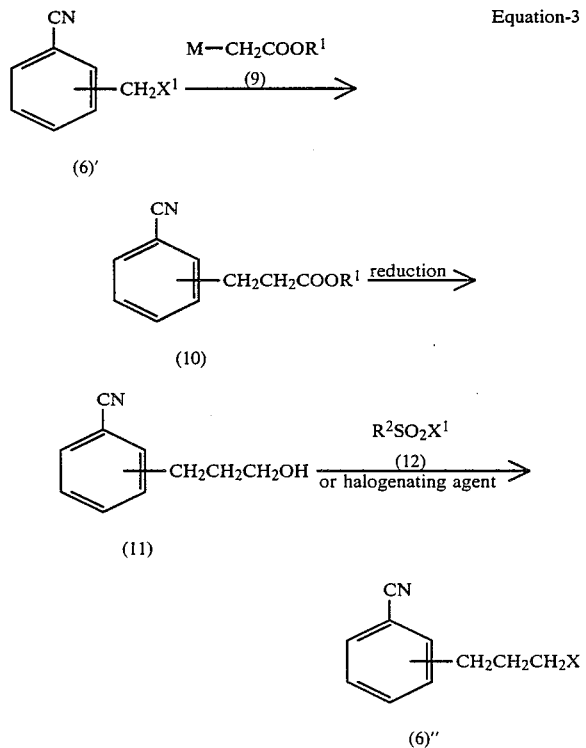

In the above equation, $R^1$ and X are as defined above, $X^1$ is a halogen atom, $R^2$ is lower alkyl, aryl or aralkyl, and M is a metal atom.

In the above equation, examples of halogen atoms are chlorine, bromine, iodine and like atoms; examples of lower alkyl groups are straight-chain or branched chain alkyl groups having 1 to 6 carbon atoms, such as methyl, ethyl, propyl, isopropyl, butyl, pentyl and hexyl; examples of aryl groups are phenyl, 2-methylphenyl, 4-methylphenyl, 4-nitrophenyl, 2-methoxyphenyl, 3-chlorophenyl and α- or β-naphthyl; examples of aralkyl groups are benzyl, 2-phenylethyl, 4-phenylbutyl, 4-methylbenzyl and 4-nitrobenzyl; and examples of metal atoms are lithium, sodium, potassium and like alkali metal atoms, magnesium and zinc atoms, etc.

The steps represented by the equation-3 will be described below in detail.

The reaction between a known compound of the formula (6)′ and a metallic enolate of acetic acid ester represented by the formula (9) is conducted in a suitable solvent, such as THF, dimethoxymethane, diglyme or like ether solvent; benzene, toluene, xylene or like aromatic hydrocarbon solvent; or DMF, DMSO, HMPA or like aprotic polar solvent, using about 1 to about 3 moles, preferably about 1 to about 1.5 moles, of the latter per mole of the former. The reaction is carried out at about −78 to about 50° C., preferably about −78 to about −30° C., for about 1 to about 5 hours, whereby a compound of the formula (10) is obtained.

The compound of the formula (10) obtained is subjected to a reduction reaction under such conditions that the ester portion of the compound (10) is converted to an alcohol without permitting the reduction of the nitrile group. More specifically, the reaction can be carried out, for example, by hydrolyzing the compound (10) to the corresponding carboxylic acid, reacting the acid with methyl chloroformate, ethyl bromoformate, isobutyl chloroformate or like alkylhalocarboxylic acid in the presence of a basic compound to obtain a mixed acid anhydride and subsequently reducing the mixed anhydride. The hydrolysis reaction of the above process can be carried out with use of a basic catalyst, such as sodium hydroxide, potassium hydroxide or calcium hydroxide, or an acid catalyst, such as formic acid, trifluoroacetic acid, trichloroacetic acid, hydrogen chloride, hydrogen bromide, p-toluenesulfonic acid or camphorsulfonic acid. When the basic catalyst is used, the reaction is effected in water; methanol, ethanol, propanol, butanol or like alcohol; dioxane, THF, diglyme or like ether; or DMF, DMSO, HMPA or like aprotic polar solvent When the acid catalyst is used, the reaction is conducted advantageously in methylene chloride, chloroform, trichloroethane or like hydrocarbon halide solvent. In either case, an excess of catalyst is usually used relative to the compound (10), and the reaction is carried out at about 20 to about 100° C. for about 1 to about 48 hours. To prepare a mixed acid anhydride, the carboxylic acid obtained is reacted with an alkylhalocarboxylic acid usually by the Schotten-Baumann reaction, which is conducted under the same conditions as already described. The mixed acid anhydride thus obtained is subsequently subjected, as contained in the reaction mixture without isolation, to a reduction reaction. This reduction reaction is carried out in a suitable solvent, such as water; methanol, ethanol, propanol or like alcohol; or ether, THF, diglyme or like ether solvent; in the presence of sodium borohydride, lithium borohydride or like reducing agent at about 0 to about 50° C., preferably about 0 to about 20° C., usually for about 1 to about 12 hours. The reducing agent is used in an amount of about 1 to about 10 moles, preferably about 1 to about 3 moles, per mole of the mixed acid anhydride. The reaction affords an alcohol represented by the formula (11).

The reaction between the alcohol of the formula (11) and a compound of the formula (12) is conducted in the presence of a basic compound in a suitable solvent. Examples of useful basic compounds are sodium hydroxide, potassium hydroxide, sodium carbonate, potassium carbonate, sodium hydrogen carbonate, potassium hydrogen carbonate, silver carbonate and like inorganic bases: sodium methylate, sodium ethylate and like alcoholates triethylamine, pyridine, N,N-dimethylaniline, N-methylmorpholine, 4-dimethylaminopyridine, 1,5-diazabicyclo[4,3,0]non-5-ene (DBN), 1,8-diazabicyclo[5,4,0]undec-7-ene (DBU), 1,4-diazabicyclo[2,2,2]octane (DABCO) and like organic bases. Examples of suitable solvents are THF, dioxane, DME, diglyme and like ethers; benzene, toluene, xylene and like aromatic hydrocarbons; methylene chloride, chloroform, 1,1,2,2-tetrachloroethane and like hydrocarbon halides; etc. The compound (12) is used usually in an amount of about 1 to about 3 moles, preferably about 1 to about 1.5 moles, per mole of the alcohol (11). The reaction is carried out usually at about 0° to about 50° C., preferably about 0° to about 20° C., for about 1 to about 12 hours, whereby a compound represented by the formula (6)″ is obtained.

The compound represented by the formula (6)″ is prepared also by reacting an alcohol (11) with a suitable halogenating agent such as thionyl chloride, phosphorus oxychloride, phosphorus oxybromide, phosphorus pentaoxide, phosphorus pentabromide or the like. This reaction is conducted in a suitable solvent such as dioxane, THF or like ether, or chloroform, methylene chloride or like hydrocarbon halide, using at least 2 moles of the halogenating agent per mole of the alcohol (11). Usually the halogenating agent is used in an excessive amount. The reaction is conducted at room temperature to about 100° C., preferably room temperature to about 70° C, for about 1 to about 24 hours.

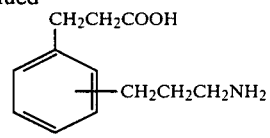

(2)′

In the above equation, $X^1$, $R^1$, $R^2$, M and X are as defined above.

In the equation-4, the reaction between a compound of the formula (A) and a compound of the formula (9) can be conducted under the same conditions as the reaction between the compound (6) and the compound (9) in the equation-3. The compound (9) is used in an amount of about 2 to about 5 moles, preferably about 2 to about 3 moles, per mole of the compound (A).

The reduction reaction of the compound of the formula (13) and the reaction of the resulting compound of the formula (14) with a compound of the formula (12) or with a halogenating agent can be carried out in the same manner as the corresponding steps shown in the equation-3.

Further a compound of the formula (2)′ is prepared from a compound of the formula (15) in the same manner as the preparation of the compound (2) from the compound (6) shown in the equation-2.

The desired compound can be obtained with a prolonged alkylene chain from the process of the equation-3, as well as of the equation-4, by suitably selecting the starting material or by repeating the reactions described by the equation.

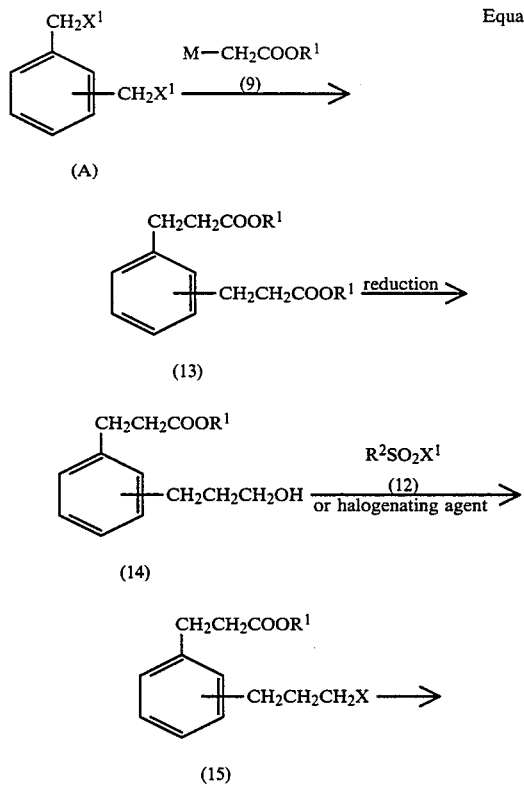

Equation-4

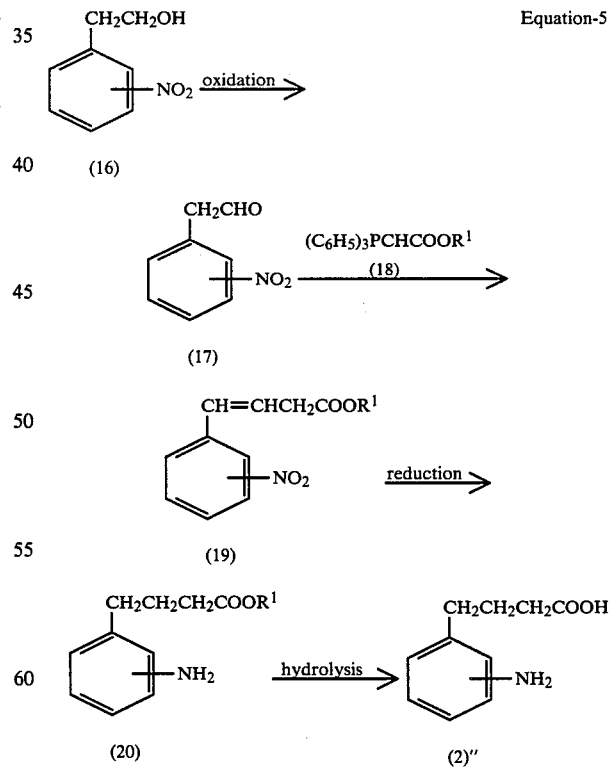

Equation-5

In the above equation, $R^1$ is as defined above.

The oxidation reaction of a compound of the formula (16) is conducted usually in a solvent with use of a suitable oxidizing agent. Examples of useful oxidizing agents are DMSO-acetic anhydride, DMSO-trifluoroacetic acid, DMSO-oxalyl chloride, DMSO-N,N'-dicyclohexylcarbodiimide, pyridinium chlorochromate, pyridinium dichromate, etc. Examples of useful solvents are benzene, toluene, xylene and like aromatic hydrocarbons and methylene chloride, chloroform and like hydrocarbon halides. The oxidizing agent is used in an amount of about 1 to about 5 moles, preferably about 1 to about 3 moles, per mole of the compound of the formula (16). The reaction is conducted usually at about 0° to about 50° C., preferably about 0° to 20° C., generally for about 5 to about 12 hours, whereby a compound of the formula (17) is obtained.

The reaction between the resulting compound of the formula (17) and a compound of the formula (18) is carried out in a suitable solvent such as diethyl ether, THF, diglyme, dioxane or like ether, benzene, toluene, xylene or like aromatic hydrocarbon, methylene chloride, chloroform or like hydrocarbon halide or DMF, DMSO, HMPA or like aprotic polar solvent. Usually about 1 to about 5 moles, preferably about 1 to about 3 moles, of the compound of the formula (18) is used per mole of the compound of the formula (17). The reaction is carried out at about 20° to about 100° C., preferably about 20° to about 50° C., for about 5 to about 12 hours, whereby a compound of the formula (19) is obtained.

The compound of the formula (19) is subjected to a reduction reaction generally in hydrogen atmosphere in methanol, ethanol, propanol, butanol or like alcoholic solvent, using a reducing catalyst such as 5% palladium-carbon or 10% palladium-carbon. Usually about 50 mg to about 1 g, preferably about 50 to about 200 mg, of the catalyst is used per gram of the compound of the formula (19). The reaction is completed in about 12 to about 72 hours at about 0° to about 50° C., preferably about 0° to about 30° C.

The compound of the formula (20) thus obtained is hydrolyzed under the same conditions as the compound of the formula (10) shown in the equation-3, whereby the desired compound represented by the formula (2)" is obtained.

The desired product obtained from the process of each of the foregoing equations can be easily isolated and purified by a usual separating method such as precipitation, extraction, recrystallization, column chromatography, preparative thin-layer chromatography or the like.

The fibrin-adsorbable protein, namely, the plasmin HC, useful for the present invention can be prepared, for example, by the method disclosed in Eur. J. Biochem., 57, 441 (1975) or the like. The plasmin HC has at least one mercapto group resulting from partial reduction of plasmin. The urokinase to be used in this invention is not limited particularly but can be any of those heretofore known, such as low-molecular-weight urokinase (LMW-UK) having an average molecular weight of 32,000, high-molecular-weight urokinase (HMW-UK) having an average molecular weight of 54,000, etc. (Biochmistry, 5, 2160 (1966).

According to the present invention, the coupling reaction between the fibrin-adsorbable protein and urokinase is carried out, for example, in an aqueous solution, physiological saline or usual buffer having a pH of 4 to 10, preferably in a buffer having a pH of 6 to 8, at 0 to 40° C, preferably around room temperature. It is desirable to conduct the reaction in a nitrogen stream. The reaction is completed usually in several minutes to about 24 hours. The buffer to be used can be any of those heretofore known and not containing ammonia or amino group.

The proportions of the fibrin-adsorbable protein, urokinase and the protein coupling reagent of the formula (1) to be subjected to the coupling reaction are suitably determined. Usually about 0.3 to about 4 moles, preferably about 0.5 to about 2 moles, of the fibrin-adsorbable protein and usually about 1 to about 50 moles, preferably about 3 to about 20 moles, of the protein coupling reagent are used per mole of urokinase.

The complex thus prepared by the process of the invention consists essentially of 1 to 5 moles, preferably about 1 mole, of urokinase and 1 mole of the fibrin-adsorbable protein as coupled therewith. After the coupling reaction, the complex can be easily isolated and purified by a usual method such as dialysis, gel filtration, fractional precipitation or affinity chromatography. The complex can be preserved when freeze-dried by the usual method.

The complex obtained by the present process is adsorbable by fibrin, has urokinase activity and is effective as a thrombolytic agent for treating thrombosis.

For use as a thrombolytic agent, the complex is formulated into pharmaceutical compositions with use of usual pharmaceutically acceptable, non-toxic carriers. Examples of useful carriers are those usually used for preparing medicinal compositions in the desired form, such as diluents and excipients including filler, extender, binder, wetting agent, disintegrator, surfactant, glazing agent, etc.

The thrombolytic compositions can be in any of various dosage forms in accordance with the contemplated purpose of treatment. Typically they are in the form of tablets, pills, powders, solutions, suspensions, emulsions, granules, capsules, suppositories, injections (solutions, suspensions, etc.).

While the thrombolytic agent can be administered in a suitable form determined according to the therapeutic purpose, it is used usually as an injection which is sterilized by the usual method and preferably made isotonic with the blood. The injection can be prepared with use of various diluents which are generally used in the art and which include, for example, water and saline. In this case, the injection may contain common salt, glucose or glycerin in an amount sufficient to form an isotonic solution. The thrombolytic compositions may have incorporated therein a usual auxiliary solubilizer, buffer, analgesic, preservative and, when desired, coloring agent, perfume, flavoring, sweetener, other drug, etc.

Although the amount of the present complex to be contained in the thrombolytic compositions is not limited particularly but is suitably variable over a wide range, it is usually about 0.01 to about 30% by weight of the whole composition.

The thrombolytic compositions are not specifically limited in the mode of administration but can be given by a suitable method in accordance with the particular form of the composition. For example, tablets, pills, solutions, suspensions, emulsions, granules and capsules are administered orally. Suppositories are given to the rectum. The thrombolytic composition in the form of an injection is given intravenously, singly or as admixed with a glucose, amino acid or like parenteral solution. The dose for human patients, which is suitably determined according to the purpose, symptoms, etc., is usually about 1,000 to about 500,000 units/kg body weight/day calculated as the effective component, i.e., fibrin-adsorbable protein-urokinase complex. The composition may be given in two to four divided doses daily.

Given below are reference examples illustrating preparation of fibrin-adsorbable protein, urokinase and protein coupling reagent useful for the present invention, examples of preparation of complexes of the invention and further examples in which some of the complexes were pharmacologically tested. The present complex was tested for various activities and other properties by the following methods.

DETERMINATION OF UROKINASE ACTIVITY (1) Synthetic substrate method (Amidolytic activity of urokinase)

A sample of urokinase is diluted to a suitable concentration with an aqueous solution containing 0.15M NaCl and 5 g/liter polyethylene glycol ("PEG 6000", product of Wako Junyaku Co., Ltd., Japan). A 800 μl quantity of 0.05M Tris.HCl buffer (pH=8.4) containing 0.1M NaCl is added to a 100 μl portion of the dilution, and the mixture is heated to 37° C. for 1 minute. A 100 μl quantity of a liquid prepared by adding 0.3 μM of substrate S-2444 (PyroGlu-Gly-Arg-p-Nitroanilide, product of AB kabi, Stockholm, Sweden) to the same buffer as above is added to the above mixture, and the resulting mixture is incubated at 37° C. for 2 minutes. A 100 μl quantity of 50% aqueous solution of acetic acid is added to the mixture to terminate the reaction, and the absorbance of the mixture is measured at 405 nm. The same procedure as above is repeated with use of standard urokinase. The activity of the sample is calculated from the absorbance measurements. The enzyme activity was expressed in International Units against the Japanese Urokinase Standard MM003.

(2) Standard fibrin plate methods (Fibrinolytic activity of urokinase)

A method: To 6 ml of 0.05M Veronal buffer (pH=8.0) containing 0.3% bovine fibrinogen (product of Poviet Production B.V., Amsterdam, Holland) and 0.1M NaCl are added final 0.02M CaCl$_2$ and final 3 NIH units/ml of bovine thrombin (product of Mochida Pharmaceutical Co., Ltd., Japan). The mixture is stirred and then scattered over a dish (8.5 cm in inside diameter) to prepare a fibrin plate. A 10 μl quantity of urokinase sample Prepared by dissolving 0.1% rabbit serum albumin (product of Sigma Chemical Company, U.S.A.) in the same buffer as above is spotted on the fibrin plate, which is then incubated at 37° C. for 16 hours. The diameter of lysis zone is thereafter measured.

B method: Two grams of fibrinogen (Fraction I; Sigma Chemical Company) is dissolved in 200 ml of 0.1M phosphate buffer (pH=7.2). One vial (1000 units) of bovine thrombin (product of Mochida Pharmaceutical Co., Ltd.) is dissolved in 200 ml of the same buffer as above, a 21 ml portion of the solution is added to a 21 ml portion of the fibrinogen solution, and the mixture is stirred to prepare a fibrin plate. The same procedure as in the A method is thereafter repeated except that bovine serum albumin (BSA) is used in place of rabbit serum albumin to determine the fibrinolytic activity of the sample in terms of the diameter of lysis zone.

QUANTITATIVE DETERMINATION OF SH GROUP

To 100 μl of deoxygenated sample is added 1 ml of deoxygenated 0.2M Tris.HCl buffer (pH=8.2). To the mixture is added 100 μl of 0.01M 5,5'-dithiobis-(2-nitrobenzoic acid) in deoxygenated methanol, the resulting mixture is stirred and then allowed to stand at room temperature for about 30 minutes, and the absorbance thereof is measured at 412 nm. The SH content of the sample was calculated using 2-mercaptoethanol as a standard.

QUANTATIVE DETERMINATION OF M-MALEIMIDOBENZOYL GROUP (MB GROUP)

To 100 μl of deoxygenated sample is added 25 μl (35 nmol) of deoxygenated aqueous solution of 2-mercaptoethanol, and the mixture is incubated at 37° C. for 20 minutes. The same procedure as followed for the quantitative determination of SH content is thereafter repeated to determine the remaining 2-mercaptoethanol content and calculate the MB group content of the sample.

SDS POLYACRYLAMIDE GEL ELECTROPHORESIS (SDS-PAGE)

A quantity of sample is admixed with the same amount of 0.02M Tris.HCl buffer (pH=8.0) containing 40% glycerol and 2% SDS (sodium dodecyl sulfonate), and the mixture is heated at 100° C. for 2 minutes. The mixture is subjected to electrophoresis using 12.5% running gel and 4% stacking gel according to the method of U.K. Laemmli et al (Nature (London), 227, 680 (1970)) or using Gradient Gel/PAA 4/30 (product of Pharmacia Fine Chemicals, Sweden). The mixture was thereafrer dyed with Coomassie Brilliant Blue R-250 (C.B.B.), and the molecular weight was measured using a standard protein (Electrophoresis Calibration Kit, product of Pharmacia Fine Chemicals).

REFERENCE EXAMPLE 1

Preparation of plasmin HC (1) Plasmin HC was prepared by the method of E. E. Rickli et al (Eur. J. Biochem., 59, 441 (1975)). A 150 mg of pure plasminogen obtained from human blood according to the method of B.A.K. Chibber et al. (Methods in Enzymology, 34, 424 (1974)) was dissolved in 0.05M Tris.HCl buffer (pH=7.8) containing 0.1M NaCl and 25% glycerol, about 3,000 units of urokinase (product of Japan Chemical Research Co., Ltd., Japan) was added to the solution, and the mixture was incubated at room temperature for 8 hours. The mixture was further incubated at room temperature for 16 hours with addition of 1,500 units of the same urokinase as above. The solution was deoxygenated by three cycles of vacuum-bleeding in nitrogen, 2-mercaptoethanol was added to the solution to a final concentration of 0.1M, and the solution was allowed to stand at 20° C. for 20 minutes. The solution was then cooled with ice and applied to a lysine-Sepharose column (5 cm in diameter and 10 cm in length) fully equilibrated with deoxygenated 0.01M sodium phosphate buffer (pH=7.2) containing 0.15M NaCl, 0.01M EDTA and 0.001M 2-mercaptoethanol. The column was then washed with about 1 liter of the same buffer solution, followed by elution with the same buffer as above which further contained 0.05M of 6-aminohexanoic acid. The fraction having a peak absorbance at 280 nm was collected and concentrated with use of Diaflo ultrafiltration membrane PM-10 (product of Amicon Corporation, U.S.A.) with application of nitrogen pressure. The same buffer as above (but not containing 2-mercaptoethanol) was added to the concentrate, and the mixture was concentrated again. This procedure was repeated several times to obtain 2-mercaptoethanol-free solution containing about 60 mg of plasmin HC, which was then deoxygenated and preserved at −80° C. The product was found to contain about 3 moles of SH groups per mole.

(2) A 300 mg quantity of pure plasminogen obtained from human blood was dissolved in 60 ml of 0.05M Tris.HCl buffer (pH=7.8) containing 0.1M NaCl and 25% glycerol, about 18,000 units of urokinase was added to the solution, and the mixture was incubated at 25° C. for 8 hours. The mixture was further incubated at 25° C. for 16 hours with addition of 9,000 units of urokinase. To the resulting solution was added a solution of 34 mg of p-nitrophenyl-p-guanidinobenzoate hydrochloride in 0.4 ml of DMF, and the combined solution was stirred at 37° C. for 10 minutes. The solution was deoxygenated by three cycles of vacuum-bleeding in nitrogen, 2-mercaptoethanol was added to the solution to a final concentration of 0.1M, and the solution was stirred at 20° C. for 20 minutes. The solution was then cooled with ice and passed through a lysine-Sepharose column (5 cm in diameter and 15 cm in length) fully equilibrated with deoxygenated 0.01M sodium phosphate buffer (pH=7.2) containing 0.2M NaCl, 0.01M EDTA and 0.001M 2-mercaptoethanol. The column was then washed with the same buffer and thereafter with 0.01M sodium phosphate buffer (pH=7.2) containing 0.001M 6-aminohexanoic acid, 0.15M NaCl, 0.01M EDTA and 0.001M 2-mercaptoethanol, followed by elution with the same buffer containing 0.003M 6-aminohexanoic acid. The fraction having a peak absorbance at 280 nm was collected and concentrated to 50 ml with use of Diaflo ultrafiltration membrane PM-10 with application of nitrogen pressure. The concentrate was passed through a Sephadex G-25 column (5 cm in diameter and 20 cm in length) which had been brought to full equilibrium with deoxygenated 0.01M sodium phosphate buffer (pH=7.2) containing 0.15M NaCl and 0.01M EDTA, followed by elution with the same buffer. The fraction having a peak absorbance at 280 nm was collected and concentrated by Diaflo ultrafiltration membrane PM-10 with application of nitrogen pressure, giving about 100 mg of plasmin HC, which was found to contain about 5 moles of SH groups per mole.

REFERENCE EXAMPLE 2

Preparation of protein coupling reagents (1) Preparation of (2S)-3-benzylthio-2-maleimidopropionic acid succinimide ester (reagent 1)

According to the method of O. Keller and J. Rudinger (Helv. Chim. Acta., 58, 531 (1975)), 6.2 g (40 mmols) of N-methoxycarbonylmaleimide was added at 0° C. to a solution of 8.44 g (40 mmols)of S-benzyl-L-cysteine in a mixture of 200 ml of saturated aqueous solution of sodium hydrogen carbonate and 100 ml of THF. The mixture was stirred for 10 minutes and then diluted with 300 ml of water and 150 ml of THF. The reaction mixture was stirred at room temperature for 30 minutes and subsequently at 40° C. for 30 minutes, neutralized with concentrated sulfuric acid and thereafter concentrated to about 200 ml in a vacuum. The concentrate was subjected to extraction with ethyl acetate, and the extract was dried over anhydrous sodium sulfate ($Na_2SO_4$) and concentrated to give a white solid. The product was subjected to silica gel chromatography (90:10:5 chloroform-ethyl acetate-acetic acid to 40:60:5 chloroform-ethyl acetate-acetic acid), giving 2.29 g of (2S)-3-benzylthio-2-maleimidopropionic acid. M.p.: 86°-87° C.

With 2.29 g (7.87 mmols) of this acid were mixed 995 mg (8.67 mmols) of N-hydroxysuccinimide and 40 ml of dimethoxyethane (DME). To this mixture was added 1.79 g (8.67 mmols) of dicyclohexylcarbodiimide (DCC) at 0° C. in argon atmosphere. The reaction mixture was stirred at 0° C. for 1 hour and then at room temperature for 3 hours and was thereafter cooled to 0° C. With addition of several drops of acetic acid, the mixture was further stirred for 1 hour. After removing the insolubles from the mixture by filtration, the filtrate was concentrated in a vacuum and then subjected to silica gel column chromatography (95:5 methylene chloride-ethyl acetate to 80:20 methylene chloride-ethyl acetate) to obtain 2.75 g (yield 90%) of the first-mentioned compound (reagent 1).

M.p.: 133°-134° C. (methylene chloride-ether)
IR (KBr): 1832, 1800, 1755, 1724 cm$^{-1}$
$^1$H-NMR (CDCl$_3$, 90 MHz): δppm=2.70 (s, 4H), 3.14 (m, 2H), 3.60 (s, 2H), 4.97 (m, 1H), 6.63 (s, 2H), 7.17 (s, 5H).
MS (m/z)=388 (M$^+$)
Found (%): C55.90, H4.03, N7.39; Calcd. for $C_{18}H_{16}O_6N_2S$ (%): C55.66, H4.15, N7.21.

(2) Preparation of (±)-4-ethylthio-2-maleimidobutyric acid succinimide ester (reagent 2)

The above compound was prepared in the same manner as in the procedure (1) from (±)-ethionine by way of (±)-4-ethylthio-2-maleimidobutyric acid.

M.p.: 57°-59° C. (methylene chloride-ether)
IR (KBr): 1838, 1800, 1752, 1725 cm$^{-1}$
$^1$H-NMR (CDCl$_3$, 90 MHz): δppm=1.20 (t, J=6.6 Hz, 3H), 2.26-2.66 (m, 6H), 2.74 (s, 4H), 5.21 (m, 1H), 6.68 (s, 2H).
MS (m/z)=340 (M$^+$)
Found: m/z=340.0736; Calcd. for $C_{14}H_{16}O_6N_2$: M=340.07290.

(3) Preparation of (4-maleimidophenyl)acetic acid succinimide ester (reagent 3)

According to the method of M. P. Cava, A. A. Deana, K. Muth and M. J. Mitchell (Org. Synth., Coll. Vol. 5, 944 (1973)), 40 ml of a solution of 10 g (66.2 mmols) of 4-aminophenylacetic acid in DMF was added to 15 ml of a solution of 7.14 g (72.8 mmols) of maleic anhydride in DMF at room temperature in argon atmosphere. The reaction mixture was stirred at room temperature for 3 hours and then diluted with 250 ml of ether-benzene (1:1). The resulting precipitate was filtered off, with which 2.87 g (35 mmols) of sodium acetate and 70 ml of acetic anhydride were admixed. The mixture was stirred at 100° C. for 1 hour in argon atmosphere and concentrated in a vacuum. The residue was diluted with 300 ml of ethyl acetate. The ethyl acetate layer was washed with saturated sodium chloride aqueous solution, dried over $Na_2SO_4$, concentrated and thereafter subjected to silica gel column chromatography (90:10:5 chloroform-ethyl acetate-acetic acid to 50:50:5 chloroform-ethyl acetate-acetic acid), giving 8.72 g (yield 57%) of (4-maleimidophenyl)acetic acid in the form of a white solid.

A 2.31 g (10 mmols) portion of the acid product thus obtained was admixed with 1.15 g (10 mmols) of N-hydroxysuccinimide and 30 ml of DME. To the mixture was added 2.27 g (11 mmols) of DCC at 0° C. in argon atmosphere, the mixture was stirred at 0° C. for 4 hours, the insolubles were filtered off, and the filtrate was concentrated and then subjected to silica gel column chromatography (80:20 chloroform-ethyl acetate) to give 2.85 g (yield 87%) of the first-mentioned compound (reagent 3).

M.p.: 153°–154° C. (methylene chloride-ether)

(4) Preparation of (2-maleimidophenyl)acetic acid succinimide ester (reagent 4)

Using appropriate starting material, the above compound (reagent 4) was prepared following the procedure of (3).

M.p.: 158°–159° C. (methylene chloride-ether)

(5) Preparation of (3-maleimidophenyl)acetic acid succinimide ester (reagent 5)

Using appropriate starting material, the above compound (reagent 5) was prepared following the procedure of (3).

M.p.: 150°–151° C. (methylene chloride-ether)

(6) Preparation of 4-maleimidomethylbenzoic acid succinimide ester (reagent 6)

To a suspension of 37 g (0.2 mol) of potassium phthalimide in 200 ml of DMF was added 50 ml of a solution of 19.6 g (0.1 mol) of α-bromo-p-tolunitrile in DMF at room temperature in argon atmosphere. The reaction mixture was stirred at 90° C. for 3 hours, then cooled to room temperature and poured into 400 ml of ice-water, followed by extraction with benzene-ether (1:1). The organic layer was washed with saturated aqueous solution of sodium chloride, dried over $Na_2SO_4$ and concentrated, giving 24.9 g (yield 95%) of 4-phthalimidomethylbenzonitrile.

Next, 26.0 g (99 mmols) of 4-phthalimidomethylbenzonitrile prepared in the same manner as above was admixed with 6.32 ml (0.129 mol) of hydrazine hydrate and 300 ml of methanol. The mixture was refluxed for 1 hour, cooled to room temperature and concentrated. The residue was dissolved in 300 ml of 1 mol $dm^{-3}$ NaOH, followed by extraction with ether. The ethereal layer was washed with saturated aqueous solution of sodium chloride, dryed over $MgSO_4$ and concentrated, affording 11.8 g (yield 90%) of 4-aminomethylbenzonitrile.

A 11.2 g (86.2 mmols) portion of 4-aminomethylbenzonitrile was admixed with 86.2 ml of aqueous solution of 3 mol $dm^{-3}$ KOH and 100 ml of THF. The mixture was refluxed in argon atmosphere for 24 hour, cooled to room temperature and then concentrated to about 100 ml. The concentrate was neutralized with concentrated hydrochloric acid, and the resulting white crystals were filtered off, giving 11.2 g (yield 86%) of 4-aminomethyl-benzoic acid.

A 3.02 g (20 mmols) portion of 4-aminomethylbenzoic acid was admixed with 100 ml of saturated aqueous solution of $NaHCO_3$, and 3.1 g (20 mmols) of methoxycarbonylmaleimide was added to the mixture at 0° C. After stirring the mixture at 0° for 10 minutes, 200 ml of water was added thereto. The mixture was then stirred at 30° C. for 1 hour and thereafter adjusted to a pH of 2 with concentrated sulfuric acid, followed by extraction with ethyl acetate. The organic layer was washed with saturated aqueous solution of sodium chloride, dried over $Na_2SO_4$ and concentrated, affording 3.18 g (yield 87%) of crude 4-maleimidomethylbenzoic acid.

To a 2.49 g (10.8 mmols) portion of the crude product were added 1.61 g (14.0 mmols) of N-hydroxysuccinimide and 50 ml of DME. To the mixture was further added 2.88 g (14.0 mmols) of DCC at 0° C. The reaction mixture was stirred at 0° C. for 1 hour and then at room temperature for 3 hours. After cooling the mixture to 0° C., several drops of acetic acid were added thereto, followed by stirring at 0° C. for 1 hour and removal of the insolubles by filtration. The filtrate was concentrated and then subjected to silica gel column chromatography (70:30 chloroform-ethyl acetate) to obtain 3.19 g (yield 90%) of the first-mentioned compound (reagent 6).

M.p.: 191°–193° C. (methylene chloride-ether).

(7) Preparation of 3-maleimidomethylbenzoic acid succinimide ester (reagent 7)

Using appropriate starting material, the above compound (reagent 7) was obtained following the procedure of (6).

M.p.: 132°–134° C. (methylene chloride-ether)

(8) Preparation of 4-(3-maleimidopropyl)benzoic acid succinimide ester (reagent 8)

To a mixture of 10.2 ml (73 mmols) of diisopropylamine and 35 ml of THF was added 27.5 ml (66 mmols) of hexane solution (2.4 mol $dm^{-3}$ solution) of butyl lithium at 0° C. in argon atmosphere, and the mixture was stirred for 15 minutes and then cooled to −78° C. With addition of 20 ml of a solution of 8.07 ml (60 mmols) of t-butyl acetate in THF, the mixture was stirred for 30 minutes. Subsequently 30 ml of THF solution of 9.8 g (50 mmols) of α-bromo-p-tolunitrile was added. After stirring the mixture at −78° C. for 1 hour, 20 ml of saturated aqueous solution of $NH_4Cl$ was added to the mixture. The resulting mixture was heated to room temperature and diluted with 100 ml of water, followed by extraction with ether. The extract was dried over $MgSO_4$ and concentrated to obtain an oil, which was subjected to silica gel column chromatography (90:10 hexane-ethyl acetate to 60:40 hexane-ethyl acetate), giving 9.8 g (yield 85%) of 4-(2-t-butoxycarbonylethyl)-benzonitrile in the form of an oil.

A 2.31 g portion of 4-(2-t-butoxycarbonylethyl)-benzonitrile was admixed with 3 ml of trifluoroacetic acid and 30 ml of methylene chloride. The mixture was stirred at room temperature for 13 hours and concentrated. The resulting concentrate was subjected to azeotropic distillation with use of toluene, giving 1.75 g (yield 100%) of crude 4-(2-hydroxycarbonylethyl)benzonitrile. This compound was used for the subsequent reaction without purification.

A 3.27 g (18.7 mmols) quantity of crude 4-(2-hydroxycarbonylethyl)benzonitrile was admixed with 2.86 ml (20.6 mmols) of triethylamine and 40 ml of THF. To the mixture was added 1.96 ml (20.5 mmols) of ethyl chloroformate at 0° C. After stirring the reaction mixture at room temperature for 3 hours, the insolubles were filtered off. The filtrate was concentrated to give a yellow oil, which was then diluted with 100 ml of benzene. The benzene layer was washed with saturated aqueous solution of $NaHCO_3$, dried over $Na_2SO_4$ and concentrated to obtain a yelllow oil. This oil was dissolved in 40 ml of THF-water (8:2). To the solution was added 2.13 g (56.1 mmols) of NaBH$_4$ at 0° C. The reaction mixture was stirred at 0° C. for 2 hours and then poured into 100 ml of 3 mol dm$^{-3}$ HCl, followed by extraction with ethyl acetate. The extract was dried over Na$_2$SO$_4$ and concentrated, giving 2.71 g (yield 90%) of 4-(3-hydroxypropyl)benzonitrile in the form of an oil.

A 16.1 g (0.1 mol) quantity of 4-(3hydroxypropyl)benzonitrile was admixed with 27.8 ml (0.2 mol) of triethylamine and 300 ml of methylene chloride. To the mixture was added 15.5 ml (0.2 mol) of methanesulfonyl chloride at 0° C. The reaction mixture was stirred at room temperature for 12 hours and then concentrated. The concentrate was diluted with 500 ml of benzene, and washed with saturated aqueous solution of sodium chloride. The washed dilution was dried over Na$_2$SO$_4$ and concentrated, giving 24.0 g (yield 100%) of crude 4-(3-mesyloxypropyl)benzonitrile in the form of an oil.

To 100 ml of DMF suspension of 21.1 g (0.114 mol) of potassium phthalimide was added 50 ml of DMF solution of 13.6 g (57 mmols) of crude 4-(3-mesyloxypropyl)benzonitrile. The reaction mixture was stirred at 90° C. for 3 hours, then cooled to room temperature and poured into 200 ml of ice-water, followed by extraction with ether-benzene (1:1). The organic layer was dried over Na$_2$SO$_4$ and concentrated, giving 14.0 g (yield 85%) of 4-(3-phthalimidopropyl)benzonitrile.

M.p.: 138°–140° C.

To a 10 g (30 mmols) portion of 4-(3-phthalimidopropyl)benzonitrile were added 1.89 ml (39 mmols) of hydrazine hydrate and 130 ml of methanol, and the mixture was refluxed for 3 hours, cooled to room temperature and then concentrated. The residue was dissolved in 200 ml of 1 mol dm$^{-3}$ NaOH, followed by extraction with ether. The extract was dried over K$_2$CO$_3$ and concentrated, giving 4.32 g (yield 90%) of 4-(3-aminopropyl)benzonitrile.

M.p.: 72°–74° C.

A 5.34 g quantity of 4-(3-aminopropyl)-benzonitrile thus obtained was mixed with 30 ml of 3 mol dm$^{-3}$ KOH and 30 ml of ethanol, and the mixture was refluxed for 24 hours, cooled to room temperature and then concentrated to remove a major portion of the ethanol. The aqueous layer was neutralized with concentrated hydrochloric acid. The precipitate separating out was filtered off, giving 4.36 g (yield 73%) of 4-(3-aminopropyl)benzoic acid. This compound was used for the subsequent reaction without purification.

A 900 mg (5 mmols) portion of 4-(3-aminopropyl)-benzoic acid was dissolved in saturated aqueous solution of NaHCO$_3$ to obtain 25 ml of a solution, to which 750 mg (5 mmols) of methoxycarbonylmaleimide was added at 0° C. The mixture was stirred at 0° C. for 10 minutes and then diluted with 50 ml of water. The dilution was stirred at 30° C. for 1 hour and then subjected to aftertreatment in the usual manner, giving 907 g (yield 70%) of crude 4-(3-maleimidopropyl)benzoic acid.

A 3.86 g (14.9 mmols) portion of this crude product was admixed with 2.23 g (19.4 mmols) of N-hydroxysuccinimide, 3.97 g (19.4 mmols) of DCC and 100 ml of DME. The mixture was stirred at 0° C. for 1 hour and then at room temperature for 3 hours. The mixture was aftertreated in the usual manner to obtain a white solid, which was subjected to silica gel column chromatography (90:10 chloroform-ethyl acetate) to give 4.77 g (yield 90%) of 4-(3-maleimidopropyl)benzoic acid succinimide ester (reagent 8).

M.P 122°–124° C. (methylene chloride-ether)

(9) Preparation of 3-(3-maleimidopropyl)benzoic acid succinimide ester (reagent 9)

Using appropriate starting material, the above compound (reagent 9) was prepared following the procedure of (8).

M.p.: 148°–149° C. (methylene chloride-ether)

(10) Preparation of 3-[4-(maleimidopropyl)phenyl]propionic acid succinimide ester (reagent 10)

To a mixture of 200 ml of THF and 44 ml (0.315 mol) of diisopropylamine was added 168 ml (286 mmols) of hexane solution of 1.70 mol dm$^{-3}$ butyl lithium at 0° C. The mixture was stirred at 0° C. for 10 minutes and then cooled to −78° C. To the mixture was added 35 ml (260 mmols) of t-butyl acetate, followed by stirring for 1 hour. To the lithium enolate thus formed was added 300 ml of THF solution of 26.4 g (0.1 mol) of α,α'-dibromo-p-xylene. The reaction mixture was stirred at −78° C. to room temperature for 12 hours, and 100 ml of saturated aqueous solution of oxalic acid was thereafter added thereto. The organic layer was separated off and subjected to extraction with ether. The organic layer was dried over MgSO$_4$ and concentrated to obtain an oil, which was then subjected to silica gel column chromatography (90:10 hexane-ether), affording 25.0 g (yield 75%) of t-butyl 3-[4-(2-t-butoxycarbonylethyl)-phenyl]propionate in the form of an oil.

A 18.0 g (54 mmols) portion of this product was admixed with 2.05 g (54 mmols) of LiAlH$_4$ and 100 ml of THF, and the mixture was stirred at 0° C. for 1 hour and diluted with 200 ml of ether. Subsequently 10 ml of 1 mol dm$^{-3}$ NaOH was added to the dilution. After removing the insolubles by filtration, the filtrate was concentrated to obtain an oil, which was then subjected to silica gel column chromatography (80:20 hexane-ethyl acetate), giving 7.70 g (yield 54%) of t-butyl 3-[4-(3-hydroxypropyl)phenyl]propionate in the form of an oil.

With a 4.82 g (18.3 mmols) portion of t-butyl 3-[4-(3-hydroxypropyl)phenyl]propionate were admixed 5.09 ml (36.6 mmols) of triethylamine, 2.84 ml (36.6 mmols) of methanesulfonyl chloride and 50 ml of methylene chloride. The mixture was stirred at room temperature for 12 hours, concentrated and then diluted with benzene. The benzene layer was washed with saturated aqueous solution of NaCl, dried over Na$_2$SO$_4$ and concentrated, giving 6.29 g (yield 100%) of t-butyl 3-[4-(3-mesyloxypropyl)phenyl]propionate in the form of an oil. This product was used for the subsequent reaction without purification.

With this product were admixed 6.77 g (36.6 mmols) of potassium phthalimide and 100 ml of DMF. The mixture was stirred at 90° C. for 3 hours, then poured into ice water and thereafter subjected to extraction with benzene-ether (1:1). The extract was dried over Na$_2$SO$_4$ and concentrated to give a yellow oil, which was subjected to silica gel column chromatography (97:3 benzene-ethyl acetate), giving 5.75 g (yeild 80%) of t-butyl 3-[4-(3-phthalimidopropyl)phenyl]propionate in the form of an oil.

With 6.88 g (17.5 mmols) of t-butyl 3-[4-(3-phthalimidopropyl)phenyl]propionate were admixed 1.10 ml (22.8 mmols) of hydrazine hydrate and 50 ml of methanol. The mixture was refluxed for 1 hour, cooled to room temperature and then concentrated. The concentrate was dissolved in 200 ml of 1 mol dm$^{-3}$ NaOH, followed by extraction with ether. The extract was dried over K$_2$CO$_3$ and concentrated to give 4.14 g (yield 90%) of t-butyl 3-[4-(3-aminopropyl)phenyl]propionate in the form of an oil.

With this product were admixed 6 ml of trifluoroacetic acid and 50 ml of methylene chloride, and the mixture was stirred at room temperature for 48 hours and concentrated. The concentrate was subjected to azeotropic distillation with use of toluene. To the residue obtained were added 30 ml of ethanol and 18 ml of 3 mol dm$^{-3}$ KOH, and the mixture was refluxed for 24 hours, cooled to room temperature and then concentrated to remove the ethanol. The aqueous layer was neutralized with concentrated hydrochloric acid and thereafter concentrated to give 3.42 g of crude 3-4-(3-aminopropyl)phenyl]propionic acid. This crude compound was used for the subsequent reaction without purification.

This crude product was made into saturated NaHCO$_3$ solution. To the solution (90 ml) was added 2.64 g (17.5 mmols) of methoxycarbonylmaleimide at 0° C. The mixture was stirred at 0° C. for 10 minutes, then diluted with 180 ml of water, stirred at 30° C. for 1 hour and adjusted to a pH of 2 with concentrated sulfuric acid. This was followed by extraction with ethyl acetate. The extract was washed with saturated aqueous solution of NaCl, then dried over Na$_2$SO$_4$ and concentrated, giving 3.16 g (yield 70%) of 3-[4-(3-maleimidopropyl)phenyl]propionic acid.

With a 2.48 g (8.64 mmols) portion of this product were admixed 1.29 g (11.2 mmols) of N-hydroxysuccinimide, 2.31 g (11.2 mmols) of DCC and 50 ml of DME. The mixture was stirred at 0° C. for 1 hour and then at room temperature for 3 hours. The reaction mixture was cooled to 0° C. and then stirred for 1 hour with addition of several drops of acetic acid. After filtering off the insolubles, the filtrate was concentrated to give a white solid, which was subjected to silica gel column chromatography (70:30 methylene chloride-ethyl acetate), giving 3.0 g (yield 90%) of 3-[4-(3-maleimidopropyl)phenyl]propionic acid succinimide ester (reagent 10).

M.p.: 159°–160° C. (methylene chloride-ether)

(11) Preparation of 3-[2-(3-maleimidopropyl)phenyl]propionic acid succinimide ester (reagent 11)

Following the procedure of (10), the above compound (reagent 11) was prepared using appropriate starting material.

IR (neat): 1822, 1792, 1740, 1710 cm$^{-1}$ $^1$H-NMR (CDCl$_3$): δ=1.85 (m, 2H), 2.69 (s, 4H), 2.69 (m, 6H), 3.46 (t, J=6.2 Hz, 2H), 6.49 (s, 2H), 7.03 (s, 4H).

MS (m/z)=384 (M$^+$)

Found: m/z=384.1325; Calcd. for C$_{20}$H$_{20}$O$_6$N$_2$: M=384.1321.

(12) Preparation of 3-[3-(3-maleimidopropyl)phenyl]propionic acid succinimide ester (reagent 12)

Following the procedure of (10), the above compound (reagent 12) was prepared using appropriate starting material.

M.p.: 121°–122° C. (methylene chloride-ether)

(13) Preparation of 4-(2-maleimidophenyl)butyric acid succinimide ester (reagent 13)

Trifluoroacetic acid (1.31 ml, 17 mmols) and 2.7 ml (33.3 mmols) of pyridine were added to a mixture of 5.51 g (33.3 mmols) of 2-(2-nitrophenyl)ethanol, 50 ml of dimethyl sulfoxide, 50 ml of benzene and 21 g (0.1 mol) of DCC. After stirring the mixture at room temperature for 4 hours, 300 ml of aqueous solution of 8.82 g (70 mmols) of oxalic acid dihydrate was added thereto. The resulting mixture was stirred at room temperature for 30 minutes and diluted with 500 ml of ethyl acetate. The organic layer was separated off, washed with saturated NaCl, dried over Na$_2$SO$_4$ and concentrated to obtain a yellow oil. The oil was subjected to silica gel column chromatography (95:5 benzene-ethyl acetate) to obtain 2-nitrophenylacetoaldehyde in the form of an unstable oil in an amount of 4.50 g (yield 81%).

With the aldehyde (4.50 g, 27 mmols) were admixed 18.0 g (53 mmols) of methoxycarbonylmethylene-triphenylphosphorane and 100 ml of methylene chloride. The mixture was refluxed for 12 hours, cooled to room temperature and concentrated. The concentrate was subjected to column chromatography (97:3 benzene-ethyl acetate), giving 2.58 g (yield 43%) of a 60:40 mixture of methyl 4-(2-nitrophenyl)-3-butenoate and methyl 4-(2-nitrophenyl)crotonate in the form of an oil.

With a 1.71 g (7.74 mmols) portion of the nitro ester mixture obtained were admixed 200 mg of 10% Pd-C and 30 ml of methanol, and the resulting mixture was stirred at room temperature in hydrogen atmosphere for 3 days. After removing the insolubles by filtration, the filtrate was concentrated to obtain 1.0 g (yield 67%) of methyl 4-(2-aminophenyl)butyrate in the form of an oil.

With this oil (1.0 g, 5.18 mmols) were admixed 10 ml of 1 mol dm$^{-3}$ KOH and 20 ml of ethanol, and the mixture was refluxed for 12 hours, cooled to room temperature and concentrated to remove the ethanol. The aqueous layer was neutralized with 1 mol dm$^{-3}$ HCl and then concentrated, giving 1.02 g of crude 4-(2-aminophenyl)butyric acid. This crude product was used for the subsequent reaction without purification.

The crude product (1.02 g) was dissolved in saturated NaHCO$_3$ aqueous solution. To this NaHCO$_3$ aqueous solution (26 ml) was added 782 mg (5.18 mmols) of methoxycarbonylmaleimide at 0° C. The mixture was stirred at 0° C. for 10 minutes, then diluted with 50 ml of water, stirred at 30° C. for 1 hour and thereafter cooled to 0° C. With addition of several drops of acetic acid, the dilution was stirred at 0° C. for 1 hour. The insolubles were filtered off, and the filtrate was concentrated to obtain a yellow oil. The oil was subjected to TLC (70:30:0.5 ethyl acetate-chloroformacetic acid), giving 367 mg of 4-(2-maleimidophenyl)butyric acid in the form of an oil. The yield was 27% based on methyl 4-(2-aminophenyl)butyrate.

With this acid product (367 mg, 1.42 mmols) were admixed 212 mg (1.85 mmols) of N-hydroxysuccinimide, 381 mg (1.85 mmols) of DCC and 20 ml of DME. The mixture was stirred at 0° C. for 1 hour and then at room temperature for 3 hours. The reaction mixture was cooled to 0° C. and then stirred at 0° C. for 1 hour with addition of several drops of acetic acid. After removing the insolubles by filtration, the filtrate was concentrated to obtain a yellow oil, which was subjected to TLC (70:30 chloroformethyl acetate) to obtain 379 mg (yield 75%) of 4-(2-maleimidophenyl)butyric acid succinimide ester in the form of an oil.

IR (CHCl₃) 1808, 1780, 1745, 1708 cm$^{-1}$
¹H-NMR (CDCl₃): δ=2.94 (m, 2H), 2.46 (m, 4H), 2.69 (s, 4H), 6.69 (s, 2H), 7.23 (m, 4H).
MS (m/z)=356 (M+)
Found: m/z=356.1006; Calcd. for $C_{18}H_{16}O_6N_2$: M=356.1008.

(14) Preparation of 4-(3-maleimidophenyl)butyric acid succinimide ester (reagent 14)

Following the procedure of (13), the above compound (reagent 14) was prepared as an oil using appropriate starting material.

IR (CHCl₃): 1808, 1780, 1743, 1718 cm$^{-1}$
¹H-NMR (CDCl₃): δ=2.02 (m, 2H), 2.63 (m, 4H), 2.73 (s, 4H), 6.69 (s, 2H), 7.06 (m, 4H).
MS (m/z)=356 (M+)
Found: m/z=356.1006; Calcd. for $C_{18}H_{16}O_6N_2$: M=356.1008.

(15) Preparation of 12-maleimidododecanoic acid succinimide ester (reagent 15)

A mixture of 4.30 g (20 mmols) of 12-aminododecanoic acid, 2.0 g (20 mmols) of maleic anhydride and 200 ml of chloroform was stirred at room temperature for 2 hours and then refluxed for 5 hours. The reaction mixture was cooled to room temperature, then concentrated to about 50 ml and cooled to 0° C. The precipitate separating out was filtered off, which was used for the subsequent reaction without purification.

With the solid product were admixed 820 mg (10 mmols) of sodium acetate and 20 ml of acetic anhydride. The mixture was stirred at 90° C. for 1 hour and concentrated. The concentrate was diluted with ethyl acetate, washed with saturated aqueous solution of NaCl, dried over Na₂SO₄ and concentrated to obtain a yellow semi-solid product, which was then dissolved in THF (30 ml)-H₂O (50 ml)-CH₃COOH (10 ml). The solution was stirred at room temperature for 1 hour and then concentrated, followed by extraction with ethyl acetate. The extract was dried over Na₂SO₄, concentrated and co-evaporated with toluene to obtain a yellow solid, which was then subjected to silica gel column chromatography (90:10:0.5 benzene-ethyl acetate-acetic acid to 70:30:0.5 benzene-ethyl acetate-acetic acid) to give 1.23 g of a white solid. The solid (1.23 g, 4.32 mmols) was admixed with 595 mg (5.18 mmols) of N-hydroxysuccinimide, 1.07 g (5.18 mmols) of DCC and 30 ml of DME. The mixture was stirred at 0° C. for 1 hour and then at room temperature for 3 hours and was thereafter cooled to 0° C. With addition of several drops of acetic acid, the mixture was further stirred at 0° C. for 1 hour. The insolubles were removed by filtration. The filtrate was concentrated to obtain a white solid, which was subjected to silica gel column chromatography (2:1 ethyl acetatehexane), giving 1.52 g (yield 90%) of 12-maleimidododecanoic acid succinimide ester.

M.p.: 67°-68° C. (methylene chloride-ether-hexane)

Table 1 below shows the structural formulae of the reagents prepared in the foregoing examples and other known protein coupling reagents. For the known reagent listed, Table 1, column of remarks shows the references and/or manufacturers concerned.

TABLE 1

| Compound Code No. | Structural formula | Remarks |
|---|---|---|
| NS 2001 | [2-maleimidophenyl COON ester structure] | Chem. Pharm. Bull., 29, 1130 (1981) |
| NS 2002 | [3-maleimidophenyl COON ester structure] | Chem. Pharm. Bull., 29, 1130 (1981) and Pierce Chemical Co., Rockford, IL, |
| NS 2003 | [4-maleimidophenyl COON ester structure] | Chem. Pharm. Bull., 29, 1130 (1981) and Pierce Chemical Co., Rockford, IL. |
| NS 2004 | NCH₂COON | Helv. Chim. Acta., 58, 531 (1975) |
| NS 2005 | N—(CH₂)₃COON | Helv. Chim. Acta., 58, 531 (1975) |
| NS 2006 | N—(CH₂)₅COON | Helv. Chim. Acta., 58, 531 (1975) |

TABLE 1-continued

| Compound Code No. | Structural formula | Remarks |
|---|---|---|
| NS 2007 | (maleimide)-N-(CH$_2$)$_{11}$COON(succinimide) | Reagent 15 |
| NS 2008 | 3-(maleimido)phenyl-CH$_2$COON(succinimide) | Reagent 5 |
| NS 2009 | 4-(2,5-dioxo-2,5-dihydro-1H-azepin-1-yl)phenyl-CH$_2$COON(succinimide) | Reagent 3 |
| NS 2010 | 4-(2,5-dioxo-2,5-dihydro-1H-azepin-1-yl)phenyl-CH$_2$CH$_2$CH$_2$COON(succinimide) | Sigma Chemical Company |
| NS 2011 | 4-((maleimido)methyl)cyclohexyl-COON(succinimide) | Sigma Chemical Company |
| NS 2014 | 2-(maleimido)phenyl-CH$_2$COON(succinimide) | Reagent 4 |
| NS 2015 | (RS) C$_2$H$_5$SCH$_2$CH$_2$CH(N-maleimido)COON(succinimide) | Reagent 2 |
| NS 2016 | (S) C$_6$H$_5$CH$_2$SCH$_2$CH(N-maleimido)COON(succinimide) | Reagent 1 |
| NS 2019 | 3-((maleimido)methyl)phenyl-COON(succinimide) | Reagent 7 |
| NS 2020 | 4-((maleimido)methyl)phenyl-COON(succinimide) | Reagent 6 and Enzyme Immunoassay, pp 90–105, published by by Igaku Shoin, Japan (1981) |

TABLE 1-continued
| Compound Code No. | Structural formula | Remarks |
|---|---|---|
| NS 2021 | 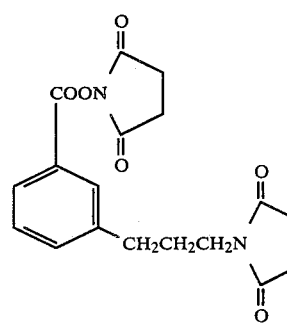 | Reagent 9 |
| NS 2022 | | Reagent 8 |
| NS 2023 | | Reagent 11 |
| NS 2024 | | Reagent 12 |
| NS 2025 | 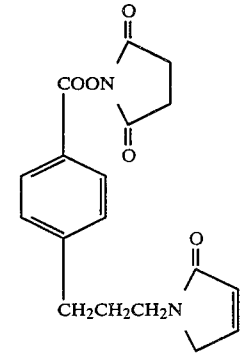 | Reagent 10 |
| NS 2026 | | Reagent 13 |
| NS 2027 | | Reagent 14 |
| NS 2028 | | C.A. Vol. 95, No 25, 219362 q |
EXAMPLE 1
(1) LMW-UK (product of Japan Chemical Research Co., Ltd., Japan) was concentrated by Diaflo ultrafiltration membrane PM-10 and then dialyzed with use of 0.01M sodium phosphate buffer (pH=7.0). The dialyzate was centrifuged (8000 r.p.m., 10 minutes). To the resulting supernatant (containing about 1 mmol of LMW-UK) was added dropwise DMF solution of 6.7 mmols of m-maleimidobenzoyl N-hydroxysuccinimide ester (compound code No. NS2002, product of Pierce Chemical Co., U.S.A., hereinafter referred to as "MBS"), and the mixture was stirred at room temperature for 30 minutes. The mixture was passed through a Sephadex G-25 fine column (1.5 cm in diameter and 20 cm in length, product of Pharmacia Fine Chemicals) equilibrated with deoxygenated 0.1M sodium phosphate buffer (pH=6.0), followed by development with the same buffer. The fraction having a peak absorbance at 280 nm was collected to obtain 0.9 mmol of LMW-UK having MB groups coupled therewith. The product had 2.7 moles of MB groups coupled to LMW-UK per mole thereof on average.

(2) A 123 mg quantity of plasmin HC obtained by the same procedure as Reference Example 1, (1) and 29.5 mg of MG group-containing LMW-UK prepared by the above procedure (1) were mixed together, deoxygenated by three cycles of vacuum-bleeding in nitrogen and stirred at room temperature for 3 hours under nitrogen. To the mixture was added 2-mercaptoethanol to a final concentration of 1 mM. The resulting mixture was stirred for 10 minutes, N-ethylmaleimide was added thereto to a final concentration of 2 mM, and the mixture was stirred at room temperature for 20 minutes. The mixture was then subjected to gel filtration using a Sephadex G-25 fine column (2.6 cm in diameter and 30 cm in length, product of Pharmacia Fine Chemicals) equilibrated and eluted with 0.1M sodium phosphate buffer containing 0.4M NaCl. The fraction having a peak absorbance at 280 nm was collected and applied to a column (2.5 cm in diameter and 5.8 cm in length) of benzamidine-CH-Sepharose (prepared by the method of L. Holmberg et al. Biochemica et Biophysica Acta, 445, 215 (1976)) equilibrated with the same buffer as above, followed by washing with 900 ml of the same buffer and then by elution with 0.1M aqueous solution of acetic acid containing 0.1M NaCl and then with 6 M aqueous solution of urea to obtain fractions having a peak absorbance at 280 nm. The fractions were subjected to gel filtration with a Sephadex G-25 column (5 cm in diameter and 25 cm in length) equilibrated with 0.1M aqueous solution of ammonium bicarbonate. The resulting protein peak fractions were applied to a lysine-Sepharose column (1.6 cm in diameter and 14 cm in length) equilibrated with 0.1M aqueous solution of ammonium bicarbonate, followed by washing with 400 ml of the same solution and with 100 ml of 0.2M aqueous solution of 6-aminohexanoic acid and by elution with 2M aqueous solution of KSCN. The protein peak fractions of the eluate were desalted and concentrated by Diaflo ultrafiltration membrane PM-10 to obtain 22.3 mg of a plasmin HC-LMW-UK complex (hereinafter referred to as "complex A").

The complex A was found to show a band with a molecular weight of 80,000 to 90,000 with use of SDS-PAGE and contained about 1 mole of plasmin HC coupled with LMW-UK per mole thereof.

EXAMPLES 2-4

Plasmin HC-LMW-UK complexes listed in Table 2 below were prepared in the same manner as in Example 1 except that the compounds listed in Table 1 were used as protein coupling reagents in place of MBS.

TABLE 2

| Example No. | Complex | Protein coupling reagent |
| --- | --- | --- |
| 2 | Complex B | Compound code No. NS 2003 |
| 3 | Complex C | Compound code No. NS 2028 |
| 4 | Complex D | Compound code No. NS 2020 |

The complexes B to D obtained were found to show a band with a molecular weight of 80,000 to 90,000 with use of SDS-PAGE and were about 1:1 in the mole ratio of LMW-UK to plasmin HC.

EXAMPLE 5

(1) LMW-UK (product of Japan Chemical Research Co., Ltd., Japan) was concentrated by Diaflo ultrafiltration membrane PM-10 and then dialyzed with use of 0.01M sodium phosphate buffer (pH=7.0). The dialyzate was centrifuged (8000 r.p.m., 10 minutes). To 1 ml portion of the resulting supernatant (containing 500,000 units/ml of LMW-UK) was added dropwise DMF solution of MBS (0.7 μmol), and the mixture was stirred at room temperature for 30 minutes. The mixture was passed through a Sephadex G-25 fine column (1.5 cm in diameter and 20 cm in length) equilibrated with deoxygenated 0.1M sodium phosphate buffer (pH=7.0), followed by development with the same buffer. The fraction having a peak absorbance at 280 nm was collected to obtain 400,000 units of LMW-UK having MB groups coupled thereto. The product had 2 moles of MB groups coupled to LMW-UK per mole thereof on average. The product was used for the reaction in the procedure (3) below.

(2) LMW-UK (product of Japan Chemical Research Co., Ltd., Japan) was concentrated by Diaflo ultrafiltration membrane PM-10 and then dialyzed with use of 0.01M sodium phosphate buffer (pH=7.0). The dialyzate was centrifuged (8000 r.p.m., 10 minutes). To 1 ml portion of the resulting supernatant (containing 500,000 units/ml of LMW-UK) was added dropwise DMF solution of MBS (4 mmols), and the mixture was stirred at room temperature for 30 minutes. The mixture was passed through a Sephadex G-25 fine column (1.5 cm in diameter and 20 cm in length) equilibrated with deoxygenated 0.1M sodium phosphate buffer (pH=7.0), followed by development with the same buffer. The fraction having a peak absorbance at 280 nm was collected to obtain 400,000 units of LMW-UK having MB groups coupled thereto. The product had 2 moles of MB groups coupled to LMW-UK per mole thereof on average. The product was used for the reaction in the procedure (3) below.

(3) An 8 mg quantity of plasmin HC obtained by the same procedure as Reference Example 1, (2) and 400,000 units (2.05 mg) of MB group containing LMW-UK prepared by the above procedure (1) or (2) were mixed together, thoroughly subjected to nitrogen replacement and stirred at room temperature for 3 hours under nitrogen. To the mixture was added 2-mercaptoethanol to a final concentration of 1 mM. The resulting mixture was stirred for 10 minutes, N-ethylmaleimide was added thereto to a final concentration of 2 mM, and the mixture was stirred at room temperature for 20 minutes. The mixture was then subjected to gel filtration using a Sephadex G-25 fine column (2.6 cm in diameter and 30 cm in length, same as above) equilibrated and eluted with 0.1M sodium phosphate buffer containing 0.4M NaCl. The fraction having a peak absorbance at 280 nm was collected and applied to a column of benzamidine-CH-Sepharose (the same as the one mentioned)) equilibrated with the same buffer as above, followed by washing with 900 ml of the same buffer and then by elution with 0.1M aqueous solution of acetic acid containing 0.1M NaCl and then with 6M aqueous solution of urea to obtain fractions having a peak absorbance at 280 nm. The fractions were combined and subjected to gel filtration with a Sephadex G-25 column (5 cm in diameter and 25 cm in length) equilibrated with 0.1M aqueous solution of ammonium bicarbonate. The resulting protein peak fractions were applied to a column of lysine-Sepharose (1.6 cm in diameter and 14 cm in length) equilibrated with 0.1M aqueous solution of ammonium bicarbonate, followed by washing with 400 ml of the same solution and by elution with 0.2M aqueous solution of 6-aminohexanoic acid. The protein peak fractions of the eluate were desalted and concentrated by Diaflo ultrafiltration membrane PM-10 to obtain 200,000 units (4.5 mg) of a plasmin HC-LMW-UK complex (hereinafter referred to as "complex E") of the invention. The complex E was found to show a band with a molecular weight of about 90,000 with use of SDS-PAGE and contained about 1 mole of plasmin HC coupled with LMW-UK per mole thereof.

EXAMPLES 6-27

Plasmin HC-LMW-HK complexes listed in Table 3 below were prepared in the same manner as in Example 5 except that the compounds given in Table 1 were used as protein coupling reagents in place of MBS.

TABLE 3

| Example No. | Complex | Protein coupling reagent |
|---|---|---|
| 6 | Complex F | Compound code No. NS 2001 |
| 7 | Complex G | Compound code No. NS 2003 |
| 8 | Complex H | Compound code No. NS 2004 |
| 9 | Complex I | Compound code No. NS 2005 |
| 10 | Complex J | Compound code No. NS 2006 |
| 11 | Complex K | Compound code No. NS 2007 |
| 12 | Complex L | Compound code No. NS 2008 |
| 13 | Complex M | Compound code No. NS 2009 |
| 14 | Complex N | Compound code No. NS 2010 |
| 15 | Complex O | Compound code No. NS 2011 |
| 16 | Complex P | Compound code No. NS 2014 |
| 17 | Complex Q | Compound code No. NS 2015 |
| 18 | Complex R | Compound code No. NS 2016 |
| 19 | Complex S | Compound code No. NS 2020 |
| 20 | Complex T | Compound code No. NS 2020 |
| 21 | Complex U | Compound code No. NS 2021 |
| 22 | Complex V | Compound code No. NS 2022 |
| 23 | Complex W | Compound code No. NS 2023 |
| 24 | Complex X | Compound code No. NS 2024 |
| 25 | Complex Y | Compound code No. NS 2025 |
| 26 | Complex Z | Compound code No. NS 2026 |
| 27 | Complex AA | Compound code No. NS 2027 |

These complexes were all found to show a band with a molecular weight of about 90,000 with use of SDS-PAGE and were about 1:1 in the molar ratio of LMW-UK and plasmin.

PHARMACOLOGICAL TESTS (1) Fibrinolytic activity test (a) The complex A obtained in Example 1 was tested for solubilizing activity by the standard fibrin plate method (A method). FIG. 1 shows the results.

In FIG. 1, amidolytic activity of urokinase or complex A (expressed in International Unit/ml against the Japanese Urokinase Standard MM003) determined by the synthetic substrate method is plotted as abscissa vs. the fibrinolytic activity (expressed in the diameter (mm) of lysis zone) determined by the standard plate method. Line (1) shows the results obtained by using the complex A, and Line (2) shows the results obtained by using LMW-UK (control).

The diagram reveals that the complex A ot the present invention is comparable to the control, i.e., LMW-UK, in fibrinolytic activity at 10 units/ml and is superior to the control in this activity at lower concentrations.

(b) Some of the complexes prepared in Examples 5 to 27 were tested for fibrinolytic activity by the standard fibrin plate method (B method). In some tests, the activity test was similarly conducted in the presence of a plasmin inhibitor.

Figure 2:
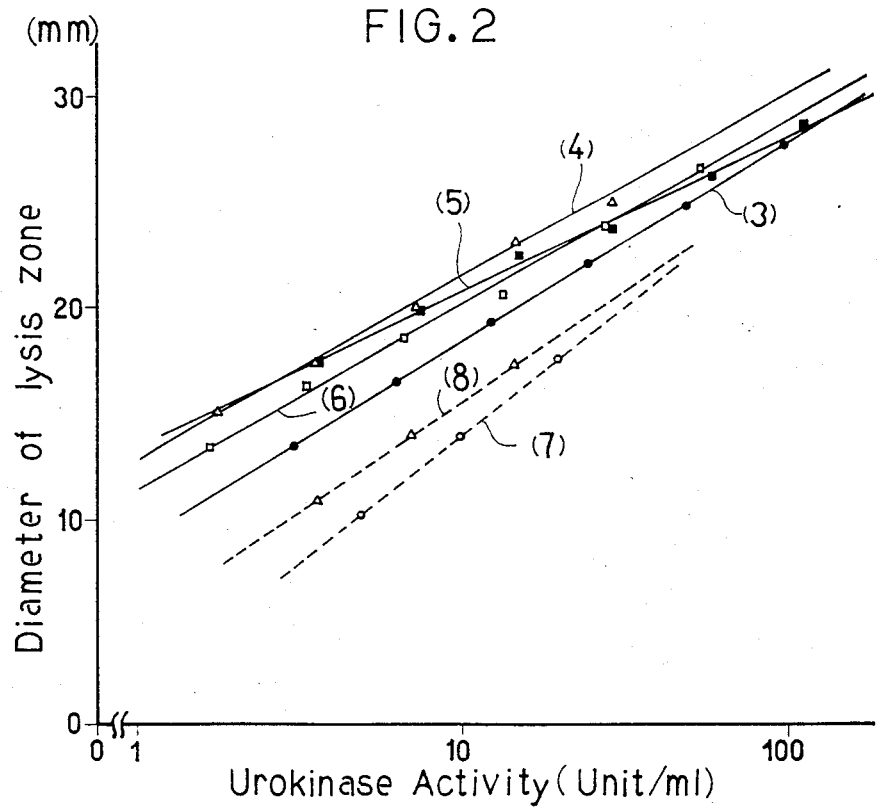

The results are shown in FIG. 2, in which the amidolytic activity (unit/ml) determined by the synthetic substrate method is plotted as abscissa vs. fibrinolytic activity (the diameter (mm) of lysis zone) determined by the standard plate method. Lines (3) to (8) in FIG. 2 represent the following.

(3): LMW-UK (control)
(4): complex E
(5): complex G
(6): complex N
(7): LMW-UK + plasmin inhibitor
(8): complex E + plasmin inhibitor The plasmin inhibitor was prepared from human plasma by the method of M. Moroi et al (J. Biol. Chem., 251, 5956 (1976)) and was used in an amount of 0.5 ml per 0.5 ml of the sample.

FIG. 2 reveals that the present complexes E, G and N retain the fibrinolytic activity and are superior to the starting material, i.e., LMW-UK in this activity at 1 to 100 units/ml and that even in the presence of the plasmin inhibitor, the complex E exhibits higher fibrinolytic activity than LMW-UK at 4 to 20 units/ml.

When similarly tested, the other complexes prepared in Examples of this invention were all found to be comparable in urokinase activity to those tested above.

(2) Test for ability to be adsorbed by fibrin (a) The complex A obtained in Example 1 was tested for ability to be adsorbed by fibrin by the following method. A column packed with 3 ml of fibrin-monomer-Sepharose 6B (prepared by the method of D. L. Heene (Thrombosis Research, 2, 137 (1973)) was brought to equilibrium with 0.005M sodium phosphate buffer (pH=7.4) containing 0.135M NaCl. The complex A, HMW-UK, plasminogen or plasmin HC (2 to 3 mg each) dissolved in the same buffer as above was applied to the column, which was then washed with 30 ml of the same buffer as above, followed by elution with the same buffer which further contained 10 mM 6-aminohexanoic acid. The ability to be adsorbed by fibrin was determined in terms of the ratio of recovery of the sample by the eluate fraction. The recovery ratios of plasminogen and plasmin HC were determined based on the absorption of the eluate fraction at 280 nm. Those of the complex A and HMW-UK were determined based on the urokinase activity of the eluate fraction determined by the synthetic substrate method.

The test results show that the ability of the complex A to be adsorbed by fibrin is 10%, which is about one-half the ability of plasminogen (24%) or about one-fourth the ability of plasmin HC (39%) and is about 10 times as high as urokinase (about 1%) in this ability.

(b) Some of the present complexes were also tested for the ability to be adsorbed by fibrin by the following method. A column packed with 20 ml of fibrin-monomer-Sepharose 6B (same as above) was equilibrated with 0.005M sodium phosphate buffer (pH=7.4) containing 0.135M NaCl. The complexes, HMW-UK or plasmin HC (0.5 mg each) dissolved in the same buffer as above was applied to the column. The column was washed with 200 ml of the same buffer, followed by elution with the same buffer containing 10 mM 6-aminohexanoic acid and with the same buffer containing 2M KSCN. The amount of the sample adsorbed by fibrin was determined based on the absorption of the eluate fraction at 280 nm for plasmin HC, or on the urokinase activity determined by the synthetic substrate method for the present complex and HMW-UK. The percentage of the amount of adsorbed sample (eluate fraction) was calculated relative to the overall recovery ratio (the adsorbed amount plus unadsorbed amount). The ability to be adsorbed by fibrin is given in terms of the percent value thus obtained. Table 4 shows the results.

TABLE 4

| | Ability to be adsorbed by fibrin |
|---|---|
| Control | |
| Plasmin HC | 95.2 |
| HMW-UK | 0 |
| Complex E | 86.0 |
| Complex O | 67.9 |

When similarly tested, the complexes of Examples other than the complexes E and O were found to be comparable to the listed complexes in the ability. These results indicate that the complexes of the invention retain the high ability to be adsorbed by fibrin attributable to plasmin HC.

(3) Curing effect on experimental pulmonary embolism in rabbits

This test was conducted according to the method of O. Matsuo et al (Nature, 291, 590 (1981)). Artificial thrombus was prepared from fresh human blood having $^{125}$I-fibrinogen admixed therewith and the $^{125}$I content thereof was measured. Then the artificial thrombus was injected into the jugular vein of an anesthetized rabbit to simulate pulmonary embolism. The complex A, or HMW-UK or physiological saline as a control was infused into the ear vein over a period of 6 hours. The blood samples were collected at time intervals and the radioactivity thereof was measured. The percentage of the radioactivity in the total blood was calculated relative to the radioactivity of the injected thrombus. Nine hours after the start of the infusion, the lungs were dissected, and the remaining radioactive thrombus was recovered from the pulmonary artery and the radioactivity thereof was measured. The percent thrombolysis was calculated based on the difference in $^{125}$I content of the injected and recovered thrombus. The total isotope recovery was measured as the sum of the radioactivity present in the recovered thrombus, the blood, the urine and the lungs, and expressed as percentage based on the radioactivity of the injected thrombus. Table 5 shows the result.

TABLE 5

| | (mean value ± SD) | | |
|---|---|---|---|
| Sample (Number of Experimental animals) | Saline (3) | Complex A (3) | HMW-UK (3) |
| Dose (urokinase activity) | — | 51700 ± 9100 units | 51100 ± 2500 units |
| Radioactivity (%) (based on injected thrombus) | | | |
| Blood 15 min | 0.70 ± 0.10 | 0.73 ± 0.36 | 0.43 ± 0.07 |
| 1 hr | 0.76 ± 0.03 | 2.41 ± 0.92 | 0.22 ± 0.09 |
| 2 hr | 0.60 ± 0.01 | 2.10 ± 0.01 | 0.50 ± 0.01 |
| 3 hr | 0.58 ± 0.05 | 1.95 ± 0.42 | 0.56 ± 0.15 |
| 4.5 hr | 0.59 ± 0.15 | 1.97 ± 0.88 | 0.56 ± 0.12 |
| 6 hr | 0.62 ± 0.02 | 2.28 ± 1.05 | 0.51 ± 0.13 |
| 7.5 hr | 0.64 ± 0.10 | 2.19 ± 1.02 | 0.55 ± 0.08 |
| 9 hr | 0.65 ± 0.10 | 2.07 ± 1.14 | 0.55 ± 1.10 |
| Urine | 2.56 ± 1.22 | 6.2 ± 0.59 | 2.10 ± 0.31 |
| Lungs | 0.21 ± 0.03 | 0.37 ± 0.37 | 0.11 ± 0.08 |
| Recovered thrombus | 97.11 ± 1.74 | 89.58 ± 1.72 | 98.58 ± 0.52 |
| Total isotope recovery (%) | 100.53 ± 0.52 | 98.26 ± 1.19 | 101.34 ± 0.51 |
| Thrombolysis (%) | 2.89 ± 1.74 | 10.42 ± 4.72 | 1.42 ± 0.52 |

Table 5 reveals that HMW-UK, when given at 50,000 units/body, produces exactly the same result as saline but that when the complex A is given at 50,000 units, significantly high blood radioactivity is maintained over the entire period with an increased amount of isotope released into the urine. The complex further achieves about 10% higher thrombolysis as determined from the radioactivity of recovered thrombus, thus exhibiting significantly high thrombolytic acitivity. The administration of the complex A entailed no tendency of bleeding.

When similarly tested, complexes B to AA were found to achieve results which are comparable to the above results.

We claim:

1. A plasmin heavy chain urokinase complex prepared by a process comprising reacting a plasmin heavy chain with urokinase in the presence of a protein coupling reagent represented by the formula

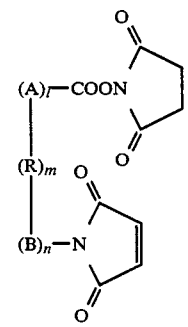

wherein R is phenylene or cycloalkylene, A is lower alkylene, B is lower alkylene which may optionally be substituted by lower alkylthio or phenyl-lower alkylthio, and l, and m and n are each 0 or 1 provided that l, m and n are not 0 at the same time.

2. A plasmin heavy chain urokinase complex as defined in claim 1 which comprises 1 to 5 moles of the urokinase and 1 mole of the plasmin heavy chain as coupled therewith.

3. A plasmin heavy chain urokinase complex as defined in claim 2 wherein the protein coupling reagent is a compound of the formula

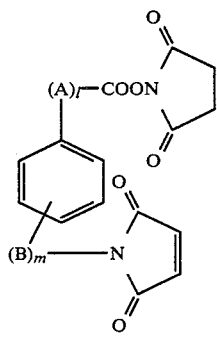

wherein A and B each represent lower alkylene, l and m each are 0 or 1.

4. A plasmin heavy chain urokinase complex as defined in claim 2 wherein the protein-coupling reagent is a compound of the formula

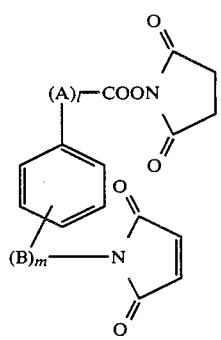

wherein A is lower alkylene, B is lower alkylene which is substituted by lower alkylthio or phenyl-lower alkylthio, and l and m are 0 or 1, and the urokinase is low molecular weight-urokinase or high molecular weight-urokinase.

5. A plasmin heavy chain urokinase complex as defined in claim 3 wherein the urokinase is low molecular weight-urokinase.

6. A plasmin heavy chain urokinase complex as defined in claim 5 prepared by the coupling reaction between the plasmin heavy chain and urokinase carried out in an aqueous solution, physiological saline or a buffer having a pH of 4 to 10 at 0° to 40° C. for several minutes to about 24 hours using about 0.3 to about 4 moles of the plasmin heavy chain and about 1 to about 50 moles of the protein coupling reagent per mole of urokinase.

7. A plasmin heavy chain urokinase complex as defined in claim 5 prepared by the coupling reaction between the plasmin heavy chain protein and urokinase carried out in an aqueous solution, physiological saline or a buffer having a pH of 4 to 10 of 0° to 40° C. for several minutes to about 24 hours using about 0.3 to about 4 moles of the plasmin heavy chain and about 1 to about 50 moles of the protein coupling reagent per mole of urokinase.

8. A plasmin heavy chain urokinase complex as defined in claim 6 prepared by the coupling reaction between the plasmin heavy chain and urokinase carried out in a buffer having a pH of 6 to 8 at room temperature for several minutes to about 24 hours using about 0.5 to about 2 moles of the plasmin heavy chain and about 3 to about 20 moles of the protein coupling reagent per mole of urokinase.

9. A plasmin heavy chain urokinase complex as defined in claim 7 prepared by the coupling reaction between the plasmin heavy chain and urokinase carried out in a buffer having a pH of 6 to 8 at room temperature for several minutes to about 24 hours using about 0.5 to about 2 moles of the plasmin heavy chain and about 3 to about 20 moles of the protein coupling reagent per mole of urokinase.

10. A plasmin heavy chain urokinase complex as defined in claim 7 which comprises 1 mole of the urokinase and 1 mole of the plasmin heavy chain as coupled therewith.

11. A plasmin heavy chain urokinase complex as defined in claim 10 which contains about 1 mole of plasmin heavy chain coupled with 1 mole of low molecular weight-urokinase wherein the protein coupling reagent is a compound of the formula

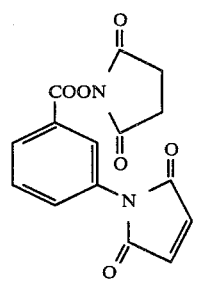

and which has a molecular weight of 80,000 to 90,000.

12. A plasmin heavy chain urokinase complex as defined in claim 10 which contains about 1 mole of plasmin heavy chain coupled with 1 mole of low molecular weight-urokinase wherein the protein coupling reagent is a compound of the formula

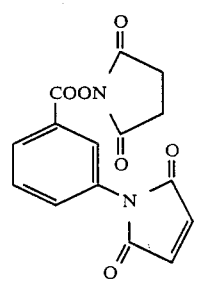

and which has a molecular weight of about 90,000.

13. A plasmin heavy chain arokinase complex as defined in claim 10 which contains about 1 mole of plasmin heavy chain coupled with 1 mole of low molecular weight-urokinase wherein the protein coupling reagent is a compound of the formula

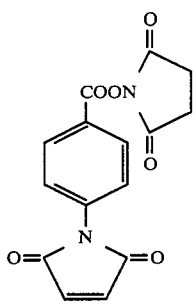

and which has a molecular weight of about 90,000.

14. A plasmin heavy chain urokinase complex as defined in claim 10 which contains about 1 mole of plasmin heavy chain coupled with 1 mole of low molecular weight-urokinase wherein the protein coupling reagent is a compound of the formula

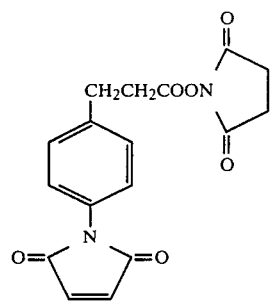

and which has a molecular weight of about 90,000.

15. A plasmin heavy chain urokinase complex as defined in claim 2 wherein R is cycloalkylene and m is 1, and the urokinase is low molecular weight-urokinase or high molecular weight-urokinase.

16. A plasmin heavy chain urokinase complex as defined in claim 2 wherein m is 0, and the urokinase is low molecular weight-urokinase or high molecular weight-urokinase.

17. A pharmaceutical composition for treating thrombosis containing the plasmin heavy chain-urokinase complex as defined in claim 1 in an amount effective for treating thrombosis in combination with a pharmaceutically acceptable, non-toxic carrier.

* * * * *